United States Patent
Crevling, Jr. et al.

[19]

[11] Patent Number: 6,069,330
[45] Date of Patent: May 30, 2000

[54] MECHANICAL SHUT-OFF AND BYPASS ASSEMBLY

[75] Inventors: Robert L. Crevling, Jr., Williamsport; Craig A. Seasholtz, Avis, both of Pa.

[73] Assignee: Shop Vac Corporation, Williamsport, Pa.

[21] Appl. No.: 09/285,803

[22] Filed: Apr. 1, 1999

Related U.S. Application Data

[60] Division of application No. 08/727,318, Oct. 8, 1996, Pat. No. 5,918,344, which is a continuation-in-part of application No. 08/678,997, Jul. 12, 1996, Pat. No. 5,850,668.

[51] Int. Cl.⁷ .......................... H01H 9/00; H01H 35/00; A47L 5/00
[52] U.S. Cl. .................. 200/84 R; 200/330; 15/DIG. 10
[58] Field of Search .................. 200/61.85–61.9, 200/318, 318.1, 318.2, 329, 330, 332, 332.1, 332.2, 84 R, 84 B, 84 C; 15/321, 353, DIG. 10, DIG. 15

[56] References Cited

U.S. PATENT DOCUMENTS

| | | |
|---|---|---|
| 2,424,657 | 7/1947 | Goodman . |
| 2,470,066 | 5/1949 | Calabrese . |
| 2,643,732 | 6/1953 | Keen . |
| 2,791,964 | 5/1957 | Reeve . |
| 2,934,623 | 4/1960 | Christensen . |
| 3,048,875 | 8/1962 | Bottinelli et al. . |
| 3,173,164 | 3/1965 | Congdon . |
| 3,303,785 | 2/1967 | Pearce . |
| 3,327,144 | 6/1967 | Double . |
| 3,345,488 | 10/1967 | Siegal . |
| 3,398,250 | 8/1968 | Bowers . |
| 3,471,663 | 10/1969 | Farrell et al. . |
| 3,496,592 | 2/1970 | Jones . |
| 3,502,825 | 3/1970 | Bailey et al. . |
| 3,614,797 | 10/1971 | Jones . |
| 3,774,260 | 11/1973 | Emus, Jr. . |
| 3,845,847 | 11/1974 | Camp ................................. 200/61.87 |
| 3,914,592 | 10/1975 | Maxey . |
| 4,021,144 | 5/1977 | Matsusaka . |
| 4,080,104 | 3/1978 | Brown, Jr. . |
| 4,087,706 | 5/1978 | Koester, Jr. . |
| 4,087,881 | 5/1978 | Bates . |
| 4,138,761 | 2/1979 | Nauta . |
| 4,153,968 | 5/1979 | Perkins . |
| 4,171,208 | 10/1979 | Lowder . |
| 4,179,768 | 12/1979 | Sawyer . |

(List continued on next page.)

FOREIGN PATENT DOCUMENTS 2246284A  1/1992  United Kingdom .

OTHER PUBLICATIONS

PCT International Search Report for International application No. PCT/US 97/12067, filed Jul. 11, 1997 (4 pages).
PCT International Search Report for International application No. PCT/US 97/18134, filed Oct. 6, 1997 (4 pages).
PCT International Search Report for International application No. PCT/US 98/00597, filed Jan. 14, 1998 (4 pages).

*Primary Examiner*—J. R. Scott
*Attorney, Agent, or Firm*—Marshall, O'Toole, Gerstein, Murray & Borun

[57] ABSTRACT

A mechanical shut-off and bypass assembly for controlling operation of a wet/dry vacuum cleaner includes a switch movable between on and off positions. A toggle member is pivotably mounted with respect to the switch and is movable to operate the switch between the on and off positions. A user operated actuator mechanism engages and manipulates the toggle member to actuate the switch. An automatic shut-off mechanism engages and manipulates the toggle member, independent of the user operated actuator mechanism, to move the switch to the off position when the liquid level in the vacuum cleaner tank reaches a preset shut-off level. The user operated actuator mechanism is operable in a bypass mode, in which the toggle member is manipulated so that the switch moves to the on position, thereby counteracting the shut-off mechanism.

20 Claims, 21 Drawing Sheets

U.S. PATENT DOCUMENTS

| | | |
|---|---|---|
| 4,198,721 | 4/1980 | Copeland .................... 200/61.85 X |
| 4,207,649 | 6/1980 | Bates . |
| 4,246,676 | 1/1981 | Hallsworth et al. . |
| 4,321,219 | 3/1982 | Barker . |
| 4,397,057 | 8/1983 | Harbeck . |
| 4,506,121 | 3/1985 | Peterson et al. ................ 200/50.28 |
| 4,675,935 | 6/1987 | Kasper et al. . |
| 4,723,337 | 2/1988 | Ellison et al. . |
| 4,776,058 | 10/1988 | Garner et al. . |
| 4,788,738 | 12/1988 | Monson et al. . |
| 4,800,612 | 1/1989 | Valentine . |
| 4,900,881 | 2/1990 | Fischer ........................... 200/61.85 |
| 4,976,850 | 12/1990 | Kulitz . |
| 5,099,543 | 3/1992 | Wade . |
| 5,120,922 | 6/1992 | Brouillette . |
| 5,134,748 | 8/1992 | Lynn . |
| 5,174,730 | 12/1992 | Nieuwkamp et al. . |
| 5,267,370 | 12/1993 | Worwag . |
| 5,430,910 | 7/1995 | Wiley . |
| 5,455,984 | 10/1995 | Blase . |
| 5,465,455 | 11/1995 | Allen . |
| 5,918,344 | 7/1999 | Crevling, Jr. et al. ................ 15/339 |

LIQUID LEVEL

June 6, 2000
6,069,330

MECHANICAL SHUT-OFF AND BYPASS ASSEMBLY

CROSS REFERENCE TO RELATED APPLICATION

This is a divisional of U.S. application Ser. No. 08/727,318, filed Oct. 8, 1996, now U.S. Pat. No. 5,918,344, which is a continuation-in-part of U.S. application Ser. No. 08/678,997, filed Jul. 12, 1996 now U.S. Pat. No. 5,850.668.

FIELD OF THE INVENTION

The present invention relates to vacuum cleaners and more particularly to wet/dry vacuum cleaners where liquid material in the tank of the vacuum cleaner is pumped out to waste.

BACKGROUND ART

Tank-type vacuum cleaners are capable of receiving dry materials such as debris or dirt and may also be used for suctioning liquids. When the tank is full, an upper vacuum assembly (which often includes a motor and an air impeller) is removed and the contents are dumped out. If the vacuum cleaner is used on liquid material, the tank, when at or near capacity, may be very heavy so that lifting the tank, to pour the contents into a sink or the like, is difficult. Even tilting the tank to pour the contents into a floor drain may be unwieldy when the liquid level in the tank is high.

One solution to the difficulties encountered in emptying liquid from vacuum tanks has been to provide an outlet at the bottom of the tank. Such a solution is satisfactory when the contents of the tank are emptied into a floor drain; however, if no floor or other low-placed drain is available the tank must be lifted to a sink or similar disposal site. In such cases the outlet at the bottom of the tank is of little value.

A second solution to emptying a vacuum tank of liquid is to provide a pump, usually with a motor located outside of or in the bottom of the tank. The pump removes liquid through a lower portion of the tank and expels it through a hose to waste. While such pumps are generally effective, they may be very costly. The pump requires not only a pump impeller and hoses but also its own electric motor, power cords, and switches. The expense of such items may be significant in the context of the overall cost of a vacuum cleaner, particularly those designed for residential use. Such pumps may also reduce the effective capacity of the vacuum tank or interfere with operation when the vacuum cleaner is used on dry materials.

SUMMARY OF THE INVENTION

In accordance with another embodiment of the present invention, the wet/dry vacuum cleaner may include a mechanical shut-off and bypass assembly. The mechanical shut-off and bypass assembly includes a switch having a first position in which power is provided to the motor and a second position in which power to the rotor is interrupted, a user operated actuator mechanism mechanically linked to the switch and capable of moving the switch to the first position or the second position, and a float mechanically linked to the switch and capable of moving the switch from the first position to the second position. The wet/dry vacuum cleaner may include a toggle member capable of engaging the switch and capable of moving the switch to the first or second position. A float transmission rod may be disposed between the toggle member and the float, putting the float transmission rod in cooperation with the toggle member and the float.

Furthermore, the toggle member of the mechanical shut-off and bypass assembly may include a locking brace having a ramp portion and a locking portion. The locking portion and the ramp portion intersect to form a critical point. The switch may include a depressible actuator, which is engageable by the locking brace and remains depressed by the locking portion once the critical point is rotated counter-clockwise past said depressible actuator.

In addition, the mechanical shut-off and bypass assembly has a cover which defines an actuator slot and the actuator mechanism includes an upper leaf spring, a lower leaf spring, a leaf connection member spanning between and connecting the upper and lower leaf spring, and a toggle actuator disposed in the actuator slot and in cooperation with the leaf connection member, whereby the upper and lower leaf spring center the toggle actuator in the actuator slot of the cover.

The actuator mechanism of the mechanical shut-off and bypass assembly may include a female connection port having an upper lip and a lower lip, and further defining a boss slot, and the toggle member may include a sidewall and a boss, the boss being connected to the sidewall and extending outward from the toggle member and into the boss slot, and the geometry of the boss slot is such that neither the upper nor lower lip of the female connection port engages the boss when the actuator mechanism is at rest.

The mechanical shut-off and bypass assembly may be employed in other apparatus. The mechanical shut-off and bypass assembly is not limited to use in a wet/dry vacuum cleaner.

Other features and advantages are inherent in the vacuum cleaner claimed and disclosed or will become apparent to those skilled in the art from the following detailed description in conjunction with the accompanying drawings.

BRIEF DESCRIPTION OF THE DRAWINGS

FIG. 17 is a perspective view of the toggle member;

DESCRIPTION OF THE PREFERRED EMBODIMENT

Figure 1:
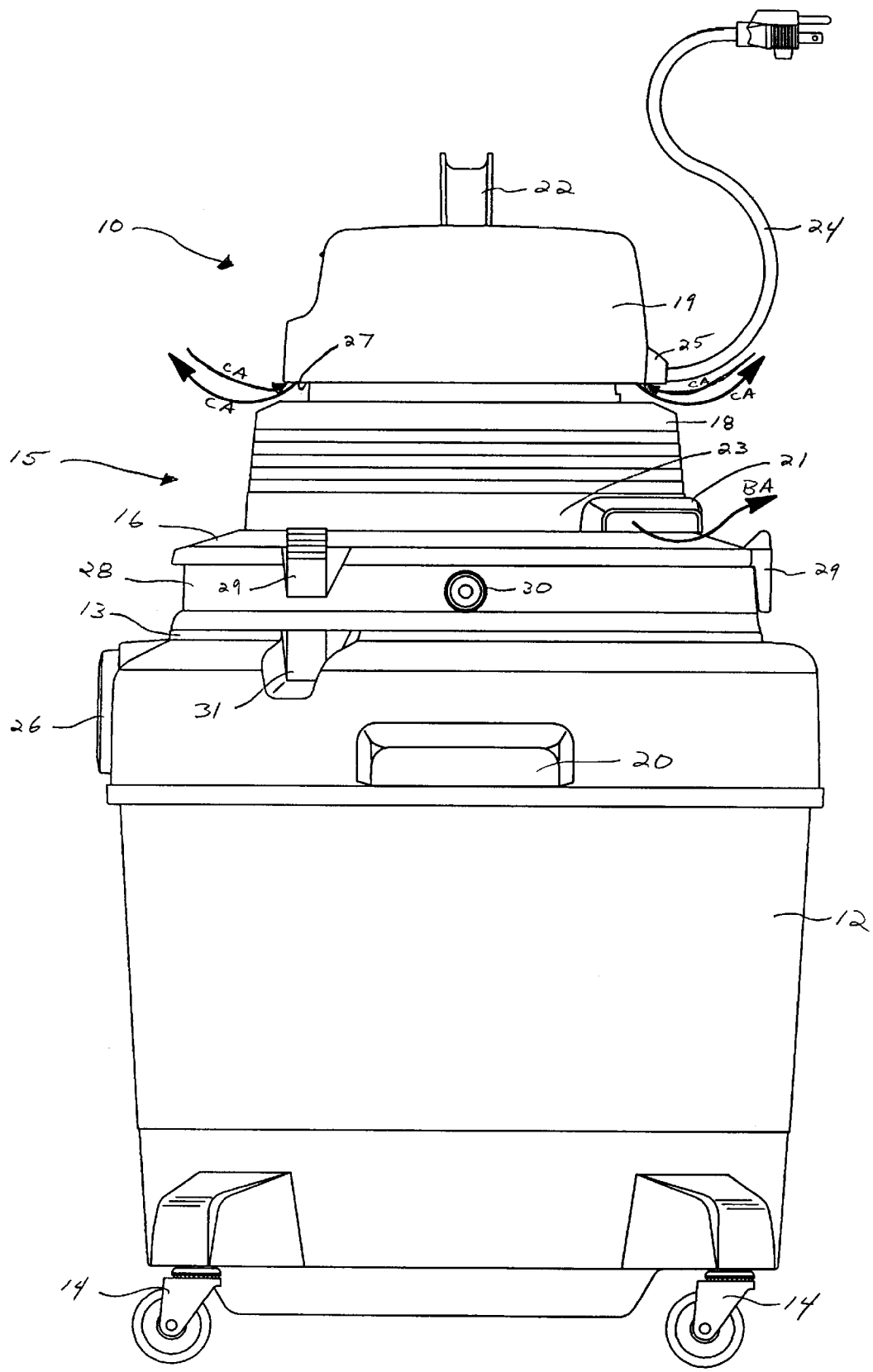
FIG. 1 is a side elevational view of a vacuum cleaner of the present invention.

Referring initially to FIG. 1, a vacuum cleaner of the present invention, indicated generally at 10, has a tank 12 supported by casters 14. The tank 12 further includes a pair of handles 20 (FIGS. 1 and 3), an inlet 26, and an upper rim 13. The handles 20 may be used to assist the user in lifting and moving the vacuum cleaner 10. The inlet 26 may be fitted with a vacuum hose (not depicted) for applying suction at desired locations.

Figure 3:
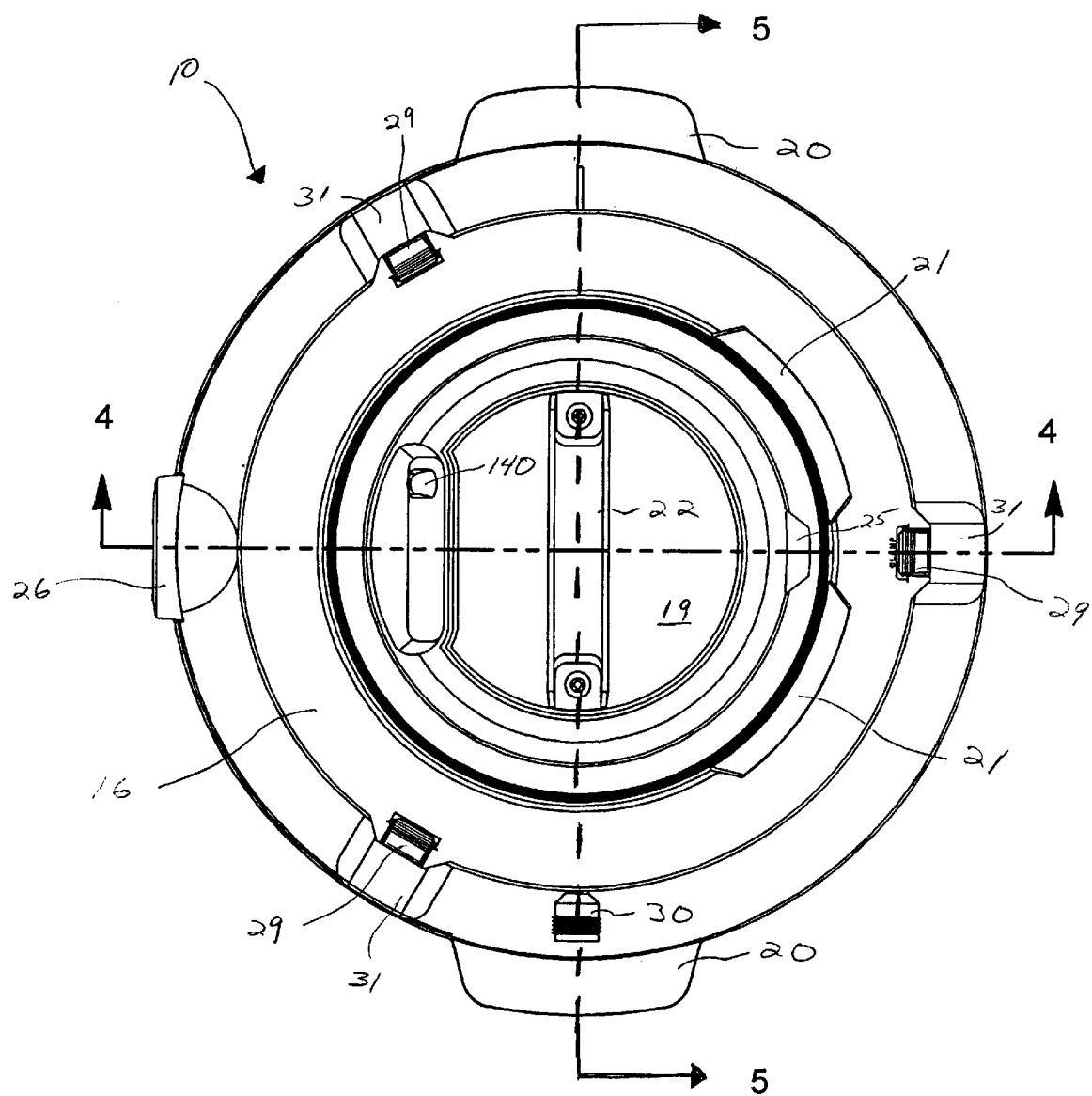
FIG. 3 is a top plan view of a vacuum cleaner of the present invention.

The tank 12 supports a removable tank extension 28. The tank extension 28 engages the upper rim 13 of the tank 12 and is disposed within the tank 12. The tank extension 28, in turn, supports an upper vacuum assembly, indicated generally at 15. The upper vacuum assembly 15 includes a lid 16, a motor housing 18, a cover 19, and a handle 22. The lid 16 is disposed above the tank extension 28 and may be attached to the tank extension 28 by one or more latches 29 which are carried by the lid 16. The latches 29 fit into tank recesses 31 when the tank extension 28 is removed. The motor housing 18 is disposed above the lid 16 and is connected to the lid 16. The motor housing 18 defines a pair of blower air discharge slots 21 (FIGS. 1 and 3). The blower air discharge slots 21 are disposed along a lower portion 23 of the motor housing 18. Air drawn into the vacuum cleaner 10 by the inlet 26 is expelled through the blower air discharge slots 21 as shown by the arrow BA in FIG. 1. The cover 19 is disposed above the motor housing 18 and is connected to the motor housing 18. The motor housing 18 and the cover 19 may be formed as two separate, detachable pieces or as one piece, integral with one another. The cover 19 includes an electric cord attachment 25. The electric cord attachment 25 connects the cover 19 to an electric cord 24 which provides power to the vacuum cleaner 10. The motor housing 18 and the cover 19 further define a cooling air opening 27. The cooling air opening 27 allows air to enter and exit under the cover 19, as shown by the arrows CA in FIG. 1. The air entering and exiting under the cover 19 circulates downward and cools a motor (not depicted) disposed within the motor housing 18. The handle 22 is disposed above the cover 19 and is connected to the cover 19.

Figure 2:
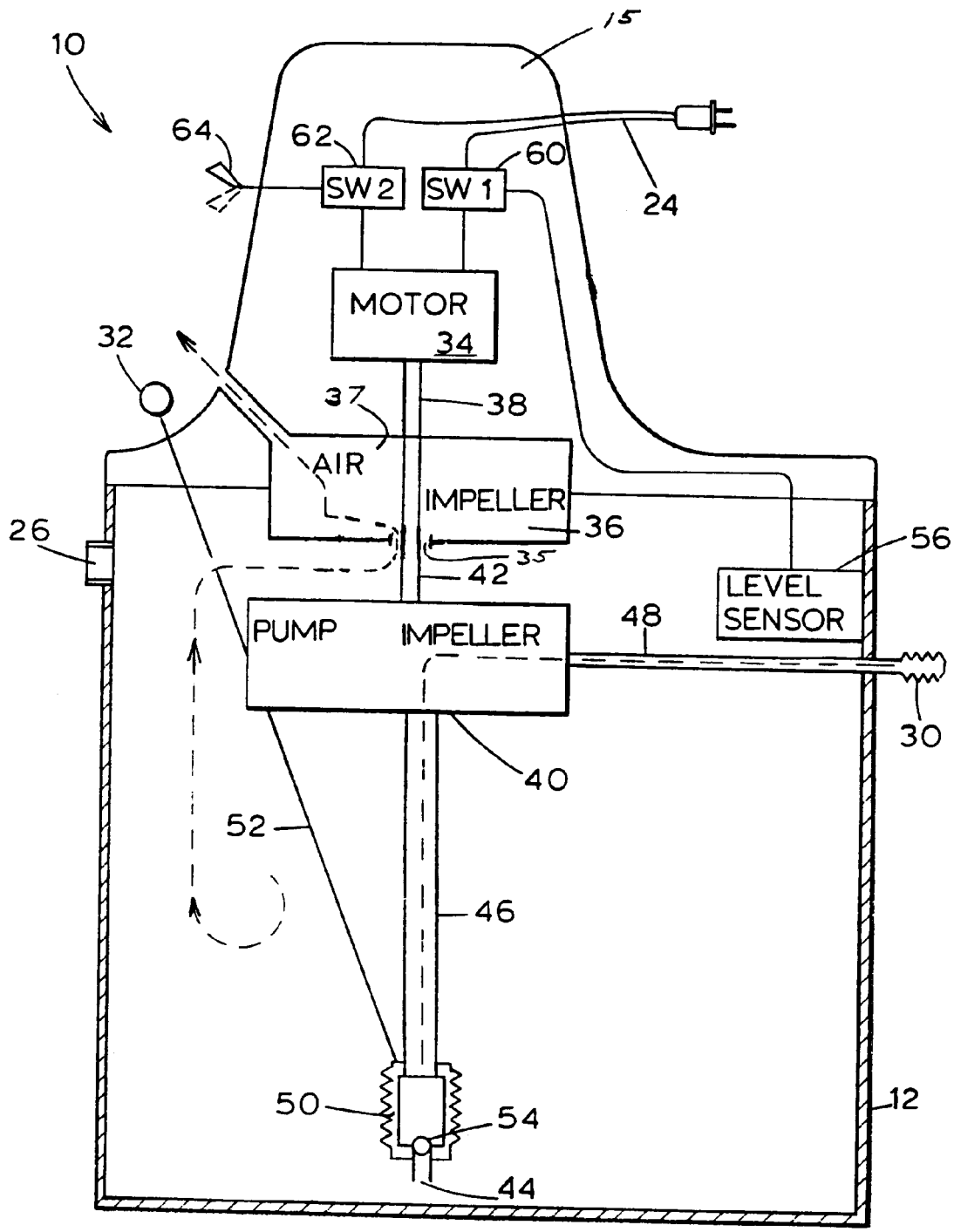
FIG. 2 is a diagrammatic view of a vacuum cleaner of the present invention.

FIG. 2 is a diagram showing the overall electrical and mechanical operation of the vacuum cleaner 10. A motor 34 drives an air impeller 36 via a shaft 38. The air impeller 36 draws air through an opening 35 in an air impeller housing 37 from the tank 12, which in turn draws air and other material through the inlet 26. Air may be expelled directly from the air impeller 36 through the upper vacuum assembly 15, or may pass through or over the motor 34 to provide cooling.

A pump impeller 40 is driven by a shaft 42 which passes through the opening 35 in the air impeller housing 37. The shaft 38 may be integral with the shaft 42 so that a unitary structure drives both the air impeller 36 and the pump impeller 40. Alternatively the shaft 42 may be separate from the shaft 38, in which case the shafts are preferably essentially collinear. As yet another alternative, the shaft 38 and the shaft 42 may not be collinear but may instead transfer torque from the motor 34 through the shaft 38 to the shaft 42 and pump impeller 40 via a transmission or gears.

The pump impeller 40 is not self-priming. A user has to manually prime the pump impeller 40 in order to pump liquid material out of the tank 12. This feature provides a significant advantage to the user. With a manual priming system, the pump only operates when the user is ready to discharge the liquid material collected in the tank 12. In other words, with the present invention, the user can vacuum up liquid material in a first location lacking a drainage source; stop vacuuming; then, move the vacuum cleaner 10 to a second location having a drainage source; manually prime the pump impeller 40; and begin pumping out the liquid material collected in the tank 12.

In order to provide priming fluid to the pump impeller 40, a bellows 50 may be compressed by use of the priming handle 32 and a priming rod 52. When liquid material enters the tank 12 it collects in the bottom of the tank 12 and enters the bellows 50 through a pump inlet 44. When there is a sufficient level of liquid material in the bellows so and the user is ready to begin pumping liquid material out of the tank 12, the user pulls on the priming handle 32 to compress the bellows 50. A check valve 54 adjacent the pump inlet 44 permits liquid to enter the bellows 50 through the pump inlet 44 but resists flow of material from the bellows 50 out through the pump inlet 44. Therefore, compression of the bellows 50 forces liquid material up through an inlet tube 46 to the pump impeller 40. When the liquid material reaches the pump impeller 40, the pump is primed. Once primed, the rotation of the pump impeller 40 draws liquid into the pump inlet 44 and through the inlet tube 46. Liquid material reaching the pump impeller 40 is discharged through an outlet tube 48 to a pump outlet 30. A hose (not depicted) may be attached to the pump outlet 30 so that liquid material removed from the tank 12 can be directed to a drain or a sink. The priming method just described is only one way envisioned to prime the pump. The present invention may be practiced with any type of pump priming system.

At times, the tank 12 will become overfilled with liquid material. A level sensor 56 may therefore be provided to detect when the level of liquid in the tank 12 is at or above a specified level. When the level sensor 56 detects liquid at or above the specified level it sends a signal to a switch 60. The switch 60, upon receiving the signal, interrupts current flowing through the electric cord 24 to the motor 34. The motor 34 and air impeller 36 thereby cease operating so that no additional liquid material enters the tank 12.

Interruption of power to the motor 34 and the air impeller 36 will also prevent the pump impeller 40 from operating if the pump impeller 40 was in operation. Under such a condition, liquid material previously collected in the tank 12 will not be removed. A switch 62 with a depressible actuator 64 is therefore provided to allow a user to override the interruption in power caused by activation of the level sensor 56. The depressible actuator 64 is biased to the "OFF" position and must be maintained in the depressed position in order for the switch 62 to provide electric power to the motor 34. While the user depresses the depressible actuator 64, the user is aware that the tank 12 is full and that the user should avoid further suctioning of additional liquid material into the tank 12 through the inlet 26. As the motor 34 continues to operate, the pump impeller 40 will also continue to operate. Continued operation of the pump impeller 40 will empty the tank to a level below the specified level for the level sensor 56 so that the switch 60 thereafter permits flow of electric power to the motor 34 without the need to depress the depressible actuator 64. A second level sensor (not depicted) may be placed at a level higher than the specified level which prevents the interruption in power from being overridden. Thus, if the user holds down the toggle while allowing additional liquid material to enter the tank 12, the second sensor will disable the motor 34 and prevent the tank 12 from overfilling. Numerous types of level sensors 56 may be used, including float sensors, proximity sensors, optical sensors, pairs of electrodes which pass current to each other through liquid in the tank when the liquid is at a sufficient height, etc.

Instead of the level sensor 56 and depressible actuator 64 shown in FIG. 2, two level sensors could be provided (not depicted). In such a system the first, lower sensor activates a light or alarm to warn the user that the tank 12 is almost full. When so notified, the user ceases suctioning additional material into the tank until the level of liquid material in the tank is lowered. If the user fails to heed the warning and the liquid level in the tank continues to rise, the second level sensor interrupts power to the motor 34.

Figure 4:
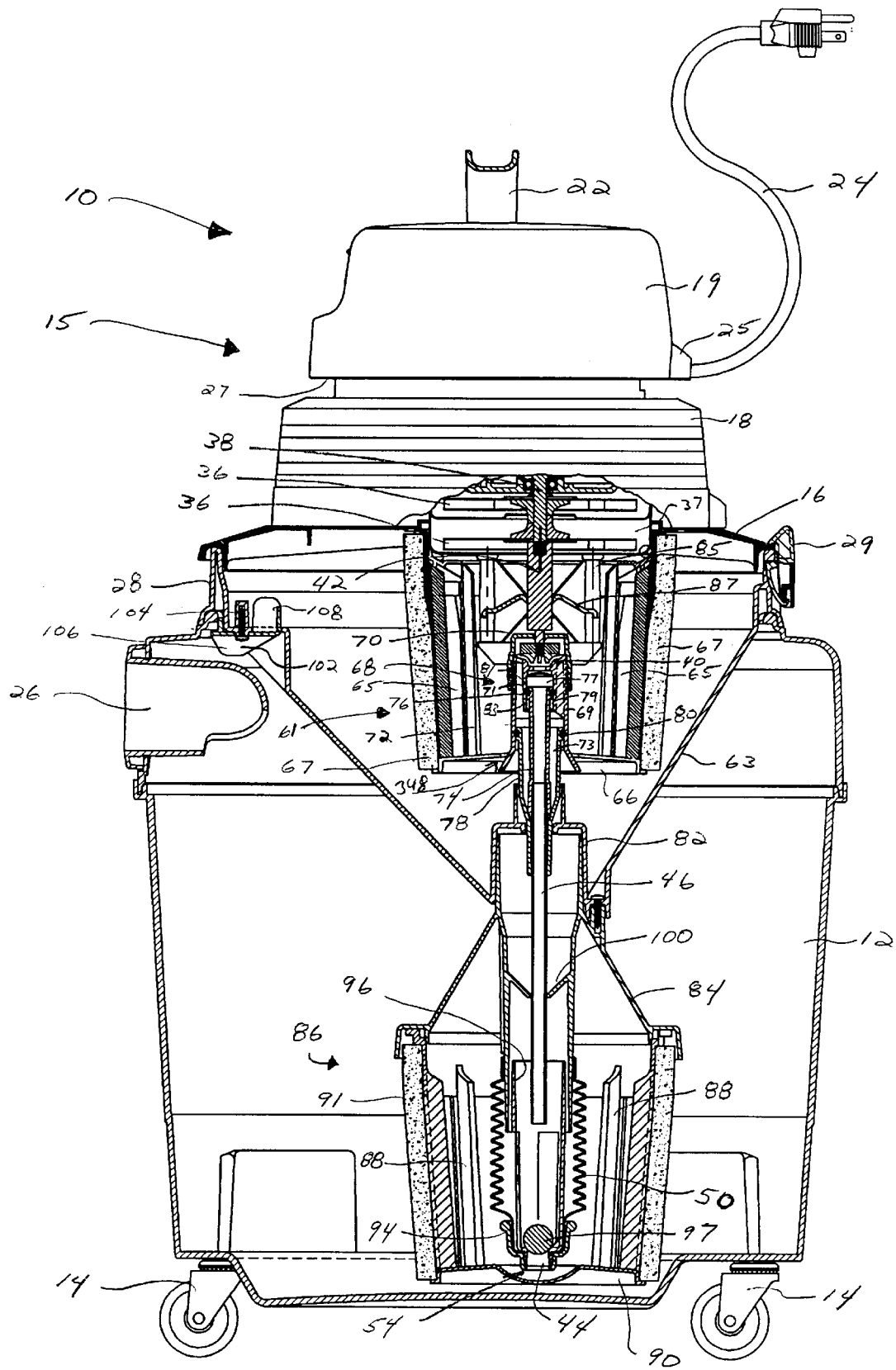
FIG. 4 is a side elevational view, partially in section along the line 4—4 in FIG. 3.
Figure 5:
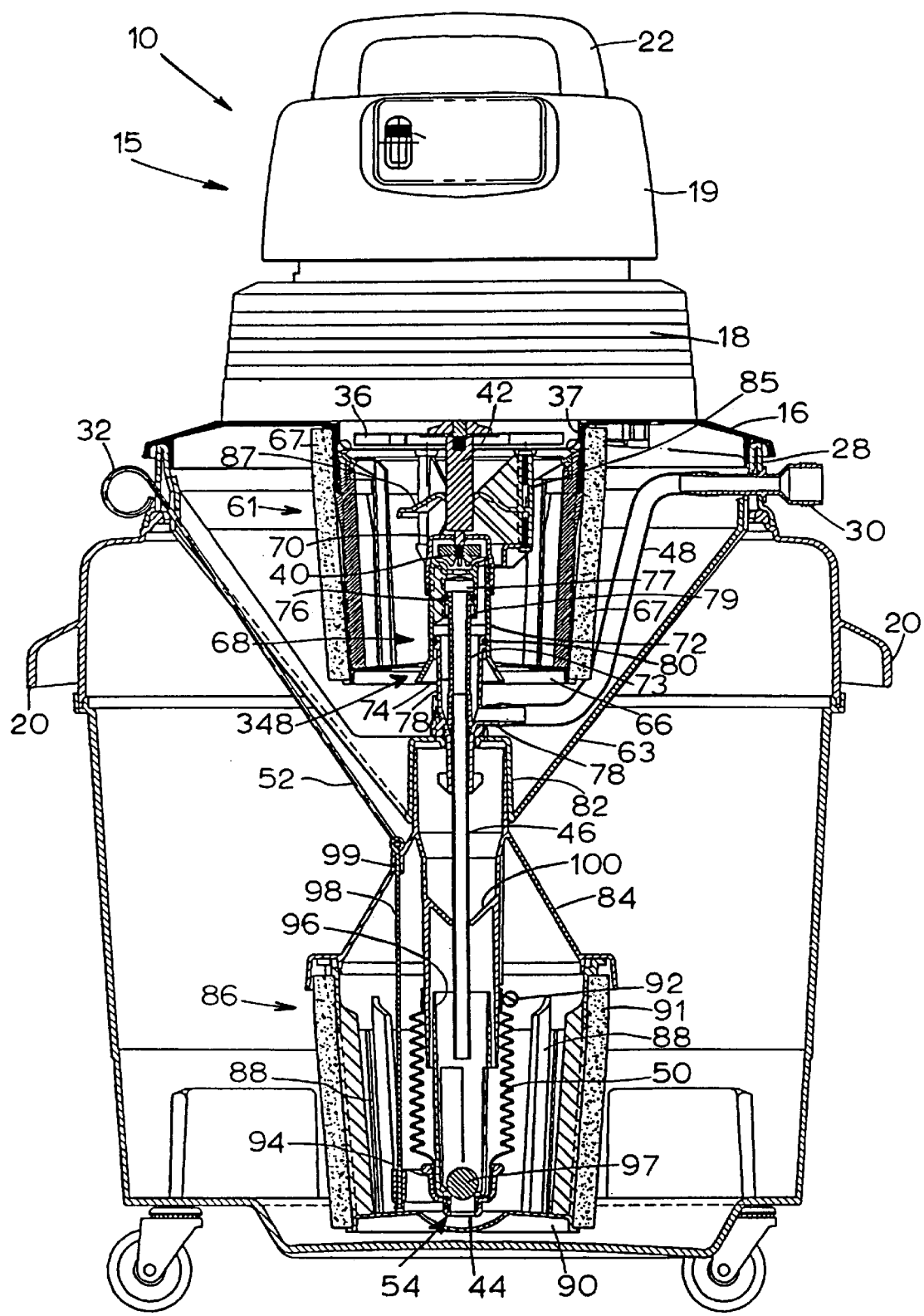
FIG. 5 is a front elevational view, partially in section, along the line 5—5 in FIG. 3.

FIGS. 4 and 5 depict the internal structure of an embodiment of the vacuum cleaner 10. The motor (not depicted) drives two air impellers 36 mounted in an air impeller housing 37 via the first axle 38. If desired, the vacuum cleaner 10 may alternatively have only a single air impeller. The air impellers 36 draw air through a lid cage indicated generally at 61, which in turn draws air through a depending portion 63 of the tank extension 28. The depending portion 63 defines several holes or slots (not depicted) which permit air flow to the air impellers 36. The lid cage 61 has several braces 65 supporting a plate 66 and surrounded by a foam filter 67. The upper vacuum assembly 15, which carries the cage 61, impellers 36, and motor, may be of conventional construction. Except for the pump and shut-off switches discussed below, the upper vacuum assembly 15 and its associated components may be identical to a Shop Vac Model QL20TS vacuum cleaner as manufactured by Shop Vac Corporation of Williamsport, Pa.

A pump indicated generally at 68 includes the pump impeller 40, which is mounted between an upper impeller housing 70 and a lower impeller housing 72. The lower impeller housing 72 includes an outer chamber wall 69 and an inner chamber wall 71, best seen in FIG. 8. The outer chamber wall 69 defines one portion of a discharge recess 73 and the inner chamber wall 71 defines an inner chamber 75. An inlet tube 74 is telescoped within the inner chamber 75. The inlet tube 74 includes a seal 76 which is disposed between the inlet tube 74 and the inner chamber wall 71. The seal 76 divides the inner chamber 75 into an upper priming chamber 77 and a lower chamber 79. The lower chamber 79 is in communication with the discharge recess 73. The inlet tube 74 is secured by any suitable means to the inlet tube 46. A pump outlet fitting 78 is telescoped within the housing 72. The pump outlet fitting 78 includes a seal 80 which is disposed between the pump outlet fitting 78 and the housing 72. The pump outlet fitting 78 defines the other portion of the discharge recess 73.

The pump impeller 40 draws liquid through the inlet tubes 46 and 74 into the upper priming chamber 77, and finally into the discharge recess 73. The liquid in the discharge recess 73 surrounds the tubes 46 and 74. The liquid then passes from the discharge recess 73 through the pump outlet fitting 78, into an outlet tube 48, and out of the tank 12 through the pump outlet 30 (FIG. 5). The seal 80 prevents liquid from escaping past the interface between the housing 72 and the pump outlet fitting 78.

When the discharge recess 73 is full with liquid, the seal 76 is surrounded by liquid. The liquid in the upper priming chamber 77 contacts a top surface 81 of the seal 76 and the liquid in the lower chamber 79 contacts a bottom surface 83 of the seal 76. Consequently, when the pump 68 is in operation, the seal 76 is surrounded by liquid on the top and bottom surfaces 81, 83. Surrounding the seal 76 with liquid is a significant advantage of the present invention. By surrounding the seal 76 with liquid, the pump 68 will not lose its prime.

In the design of other pumps, one side of a seal, equivalent to the seal 76, is in contact with air only—no liquid. In these other designs, if the seal deteriorates, the pump will lose its prime because the liquid will leak from the upper priming chamber to the air-filled lower chamber thereby allowing air to enter the upper priming chamber. Consequently, the pump, in other designs, will not function under this condition. In the present invention, however, if the seal 76 deteriorates, the pump will not lose its prime and the pump 68 will continue to function. In the present invention, both the upper priming chamber 77 and the lower priming chamber 79 are filled with liquid, and hence there is no opportunity for air to enter the upper priming chamber even when the seal deteriorates. Granted, in the present invention, the pump 68 will operate less efficiently if the seal 76 begins to deteriorate and liquid starts to leak from the upper priming chamber 77 to the lower chamber 79, but the pump 68 does not stop functioning.

The lower impeller housing 72 is attached to the upper impeller housing 70, which is in turn attached to a pump mount 85. The pump mount 85 is attached to the air impeller housing 37. The pump mount 85 also carries a water deflector 87, which inhibits water from passing into the air impellers 36. Ordinary pumps have a seal where the shaft 42 passes through the upper impeller housing 70. The pump 68 has no such seal because seals often require cooling fluid and the pump impeller 40 may rotate without any fluid in the upper impeller housing 70. A small amount of liquid will therefore pass out of the upper impeller housing 70 around the shaft 42. The water deflector 87 will direct the liquid back into the tank 12.

The pump outlet fitting 78 is mounted to an inverted cup 82 on the tank extension 28. The tank extension 28 carries an intake support 84 and a lower cage indicated generally at 86 having brackets 88 and a plate 90. The lower cage 86 may be surrounded by a foam filter 91 to prevent large particles suspended in liquid in the tank 12 from entering the pump inlet 44. The lower cage 86 also houses the priming mechanism for the pump 68, including the bellows 50, which is secured to the intake support 84 by a hose clamp 92 (FIG. 5). The lower end of the bellows 50 is captured between a bracket 94 and a cup 96. The bellows 50, bracket 94, and the cup 96 each have an opening to allow liquid material in the tank 12 to enter into the cup 96. A ball 97 seats in the cup 96 to form the check valve 54 which prevents liquid material in the cup 96 from flowing out of the cup 96 through outlet 44. A priming rod 98 (FIGS. 5 and 6) extends through a hole 99 in the intake support 84 and is attached to the priming rod 52 and to a bracket extension 94 so that upward movement of handle 32 from tank extension 28 lifts the bracket 94 and the cup 96 to compress the bellows 50.

Figure 6:
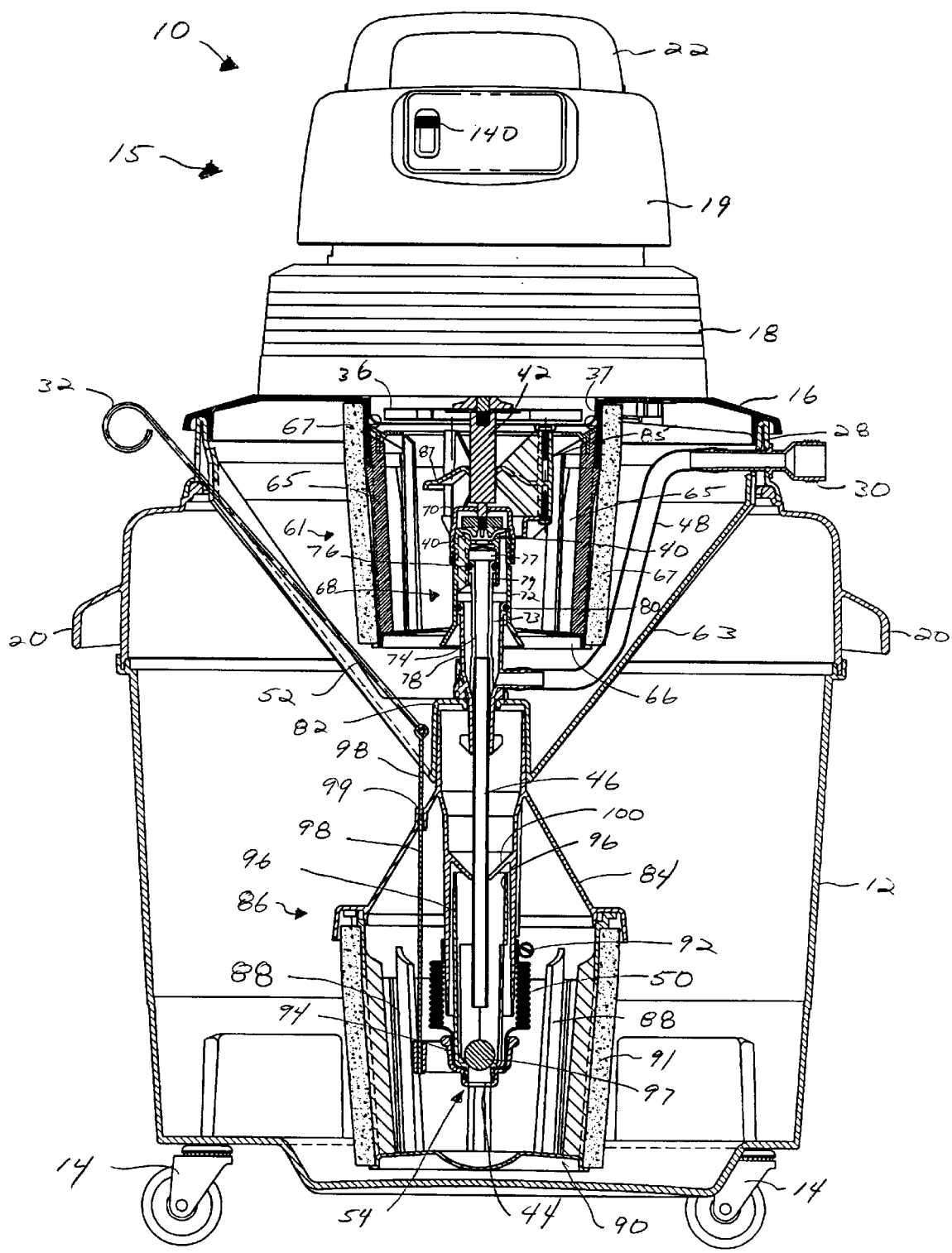
FIG. 6 is a view similar to FIG. 5 showing the pump of the vacuum cleaner being primed.

FIG. 6 depicts the cup 96 in its upper position. The cup 96 is moved upward by a user pulling the priming handle 32, thereby lifting the priming rods 52 and 98 and the bracket 94. In moving from the position of FIG. 5 to the position of FIG. 6, liquid in the cup 96 and the bellows 50 is forced up into inlet tube 46 and eventually to the pump impeller 40. A seal 100 in the intake support 84 prevents liquid and/or air in the support 84 from being pushed farther up into intake support 84 to force liquid in the cup 96 into inlet tube 46. The bellows 50 compresses when the cup 96 is in its upper position and also prevents liquid in the cup 96 from leaking back into the tank 12.

Figure 7:
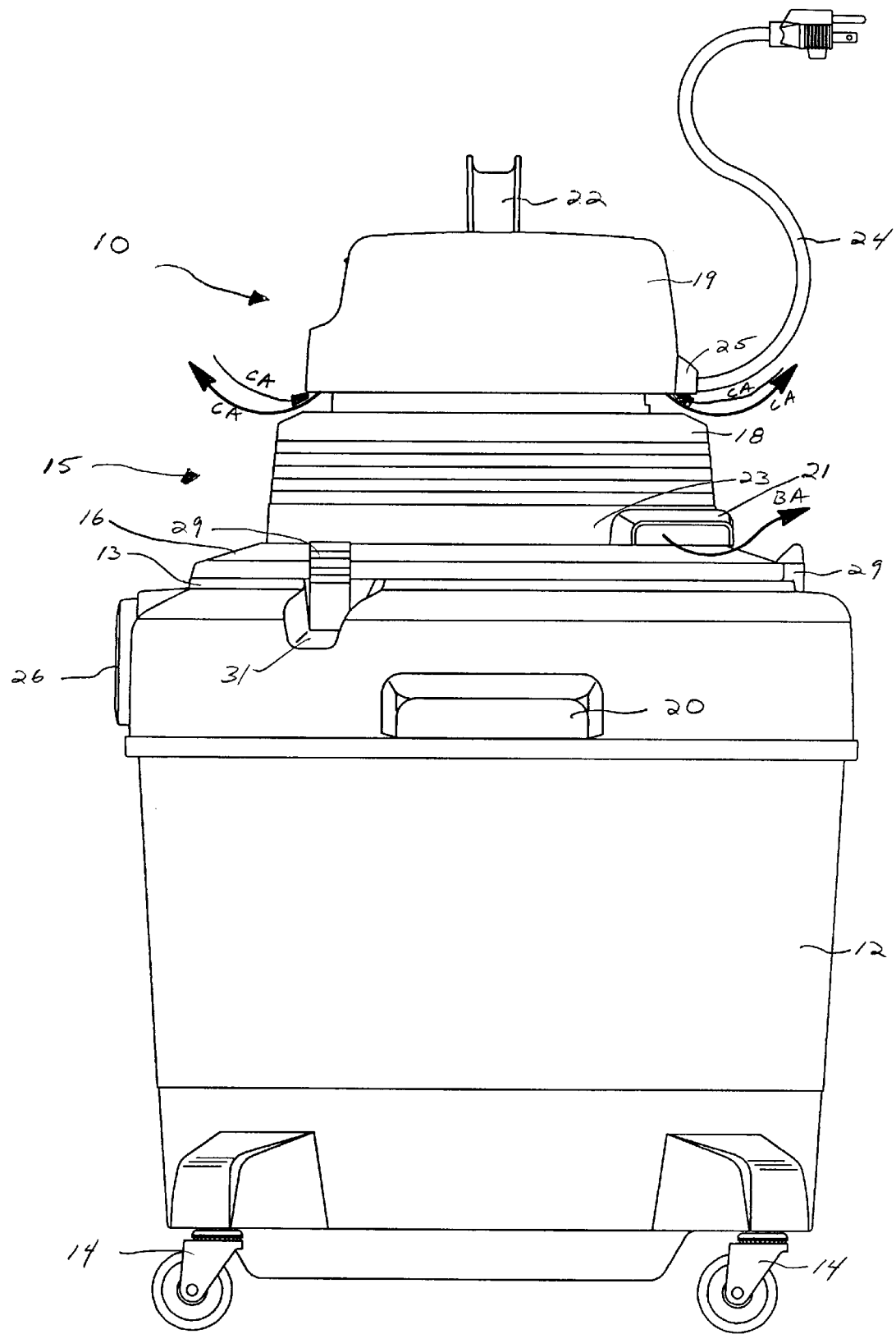
FIG. 7 is a side elevational view of a vacuum cleaner of the present invention with a tank extension removed.
Figure 8:
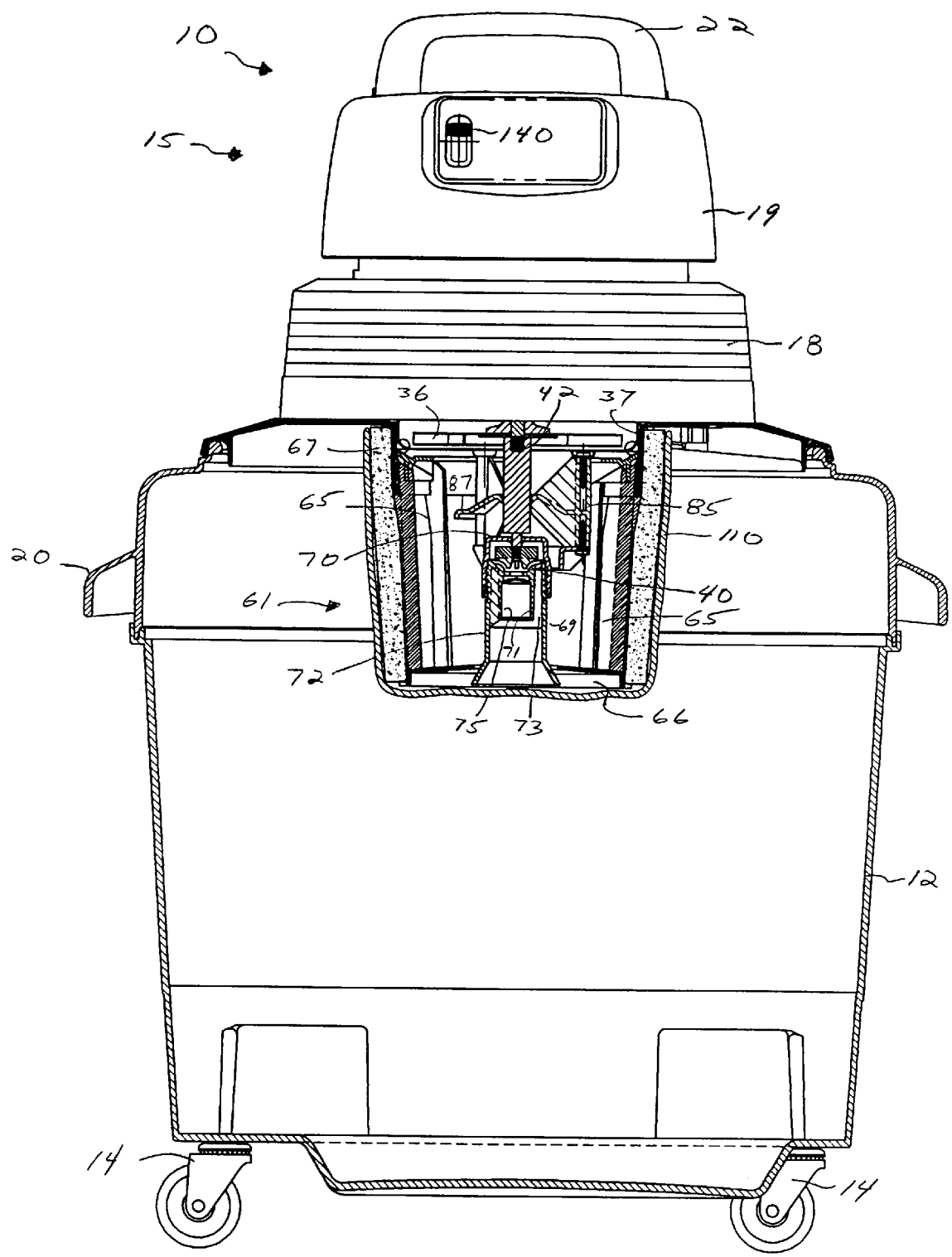
FIG. 8 is a view similar to FIG. 5 of the vacuum cleaner of FIG. 7.

FIGS. 7 and 8 depict the vacuum cleaner with the tank extension 28 (FIGS. 1 and 4–6) and its associated components removed from between the tank 12 and the upper vacuum assembly 15. By removing the tank extension 28 and the entire inlet assembly for the pump 68, the vacuum cleaner 10 is readily usable for suctioning dry material. With the tank extension 28 and its associated components removed, there is additional capacity for vacuuming dry material. Further, the removed pump inlet components will not be clogged with dry material when later used to expel liquid material from the tank 12. In addition, the openings through the tank extension 28 for the priming rod 52 and pump outlet 30, which might otherwise allow air to leak into the tank 12, are not present when the vacuum cleaner 10 is used on dry material. Thus, removability of the tank extension 28 may also increase the suctioning ability of the vacuum cleaner 10 when used on dry material.

The vacuum cleaner 10 can be used to vacuum wet or dry material with the tank extension 28 either in place or removed. With the tank extension in place (FIGS. 1–6), the vacuum cleaner 10 is advantageously configured for suctioning liquid material since that material can be readily removed from the tank 12. Similarly, with the tank extension 28 removed (FIGS. 7 and 8), the vacuum cleaner 10 is advantageously configured for suctioning dry material.

Referring once again to FIG. 4, the tank extension 28 has a latch or latches, indicated generally at 102, which are each held to the tank extension 28 by a screw 104. Each of the latches 102 has a locking arm 106 which engages an edge of the tank 12 to hold the tank extension 28 to the tank. A tab 108 on the latch 102 is accessible to a user when the lid 16 has been removed from the tank 12 and tank extension 28 by unlocking the latches 29. Rotation of the tab 108 about the screw 104 releases the tank extension 28 from the tank 12.

As can be seen by comparing FIG. 4 with FIG. 8, removal of the lid 16 from the tank extension 28 divides the pump 68 into an upper pump assembly and a lower pump assembly. The upper pump assembly includes the upper impeller housing 70, the lower impeller housing 72, the pump impeller 40, and their associated components. The lower pump assembly includes the inlet tube 74, pump outlet fitting 78, the inlet tube 46, outlet tube 48 (FIG. 5), and their associated components. All components of the upper pump assembly are attached to and, during normal operation by a user, remain with the upper vacuum assembly 15. All components of the lower pump assembly are attached to and, during normal operation by a user, remain with the tank extension 28. Therefore, when the upper vacuum assembly 15 is separated from the tank extension 28, the upper pump assembly separates from the lower pump assembly at the seals 76 and 80. The lower portion of the lower impeller housing 72 is flared to facilitate insertion of the lower pump assembly into the upper pump assembly upon reconfiguration of the vacuum cleaner 10 for removal of liquid material from the tank 12. The flared end of the lower impeller housing 72 aligns the seals 76 and 80 to provide the proper relationship of the components of the pump 68.

As seen in FIG. 8, once the tank extension 28 and its associated lower pump assembly are removed from the lid cage 61, a particulate filter 110 may be placed over the lid cage 61. The particulate filter 110 covers the plate 66 and the opening in the plate 66 through which the lower impeller housing 72 extends.

Figure 9:
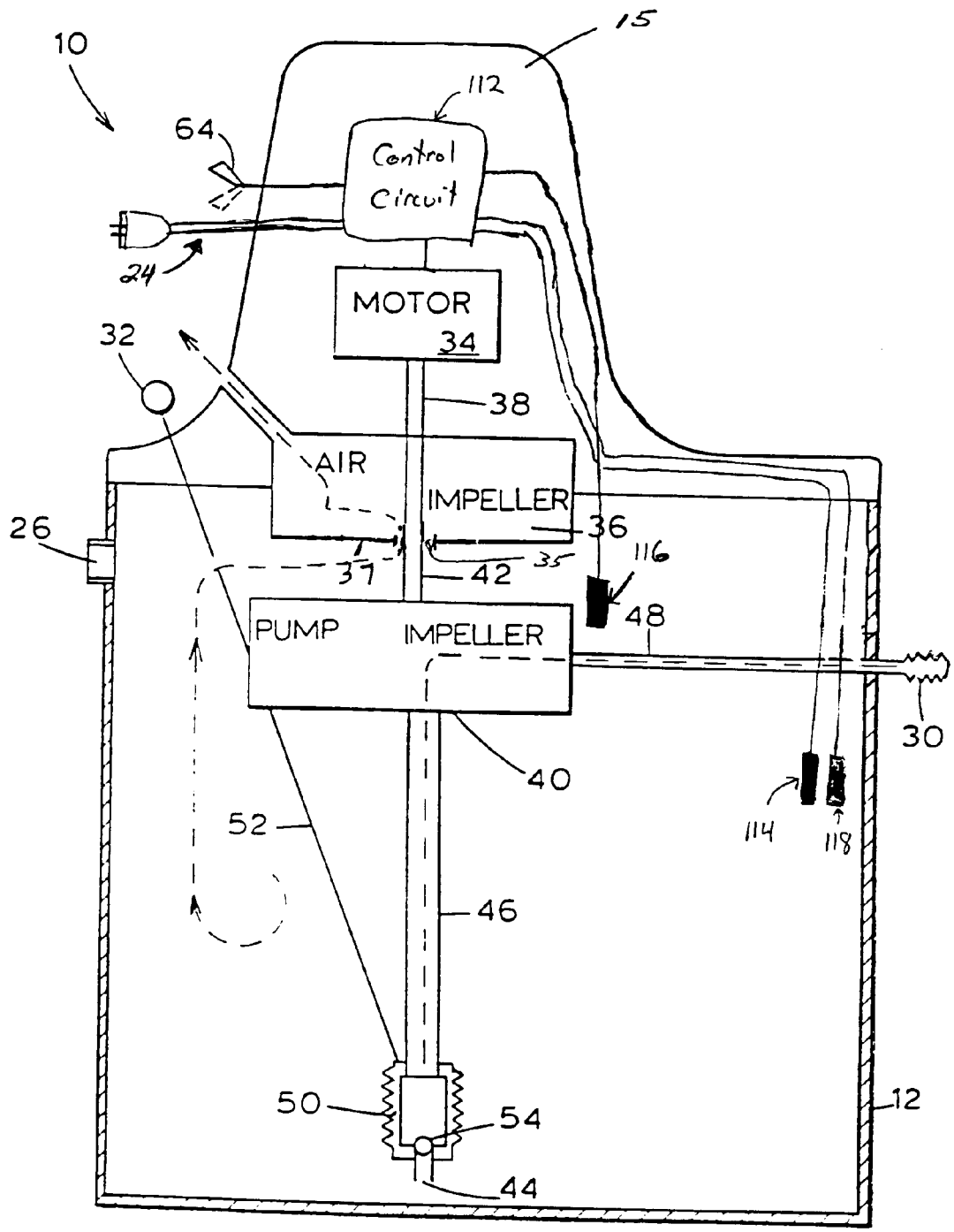
FIG. 9 is a diagrammatic view of the vacuum cleaner of the present invention configured with electrode level sensors.

FIG. 9 illustrates an embodiment of the present invention where the level sensors are electrodes. A control circuit 112 enables and disables the motor 34 based on the level of the liquid in the tank 12. The control circuit 112 also includes the depressible actuator 64 that opens and closes a switch internal to the control circuit, an electrode 114, and a further electrode 116, all of which are shown external to the control circuit 112 in FIG. 9 for clarity.

When the liquid level in the tank 12 is below the electrode 114, the control circuit 112 enables the motor 34 and the vacuum operates in normal vacuuming/pumping mode. As the user vacuums, liquid enters the tank 12 through the inlet 26 and if the pump impeller 40 is in operation, is pumped out of the tank 12 through the pump outlet 30. In the preferred embodiment, a potential-setting electrode 118 is disposed at the same particular liquid level height as the electrode 114. When the liquid level in the tank 12 reaches the potential-setting electrode 118 and the electrode 114, a conductive path is formed through the liquid between the two electrodes.

If desired, the potential-setting electrode 118 need not be disposed at the same height as the electrode 114, as a conductive path will be formed whenever the water level reaches the higher of the two.

The current passing between the electrodes 114 and 118 signals the control circuit 112 to turn off the motor 34, shutting off the air impeller 36 and the pump impeller 40. This prevents the user from vacuuming more liquid into the tank 12 and further raising the liquid level. However, it is desirable that the user be able to use the motor 34 to lower the liquid level rather than emptying the tank 12 manually. Once the motor 34 has been disabled by the control circuit 112, the user may reactivate the motor 34 by depressing the depressible actuator 64. This signals the control circuit to re-enable the motor 34, allowing a user to hold the vacuum nozzle out of the liquid and pump the liquid out of the tank 12 through the outlet 30.

If the user fails to remove the vacuum nozzle from the liquid while depressing the depressible actuator 64, the liquid level in the tank 12 may continue to rise and may contact the further electrode 116 that is disposed at a liquid level height above the electrode 114. Once liquid contacts the further electrode 116, the control circuit 112 will deactivate the motor 34. The only way to restart the motor 34 is to manually empty the tank 12 and reset the power to the control circuit 112.

Figure 10:
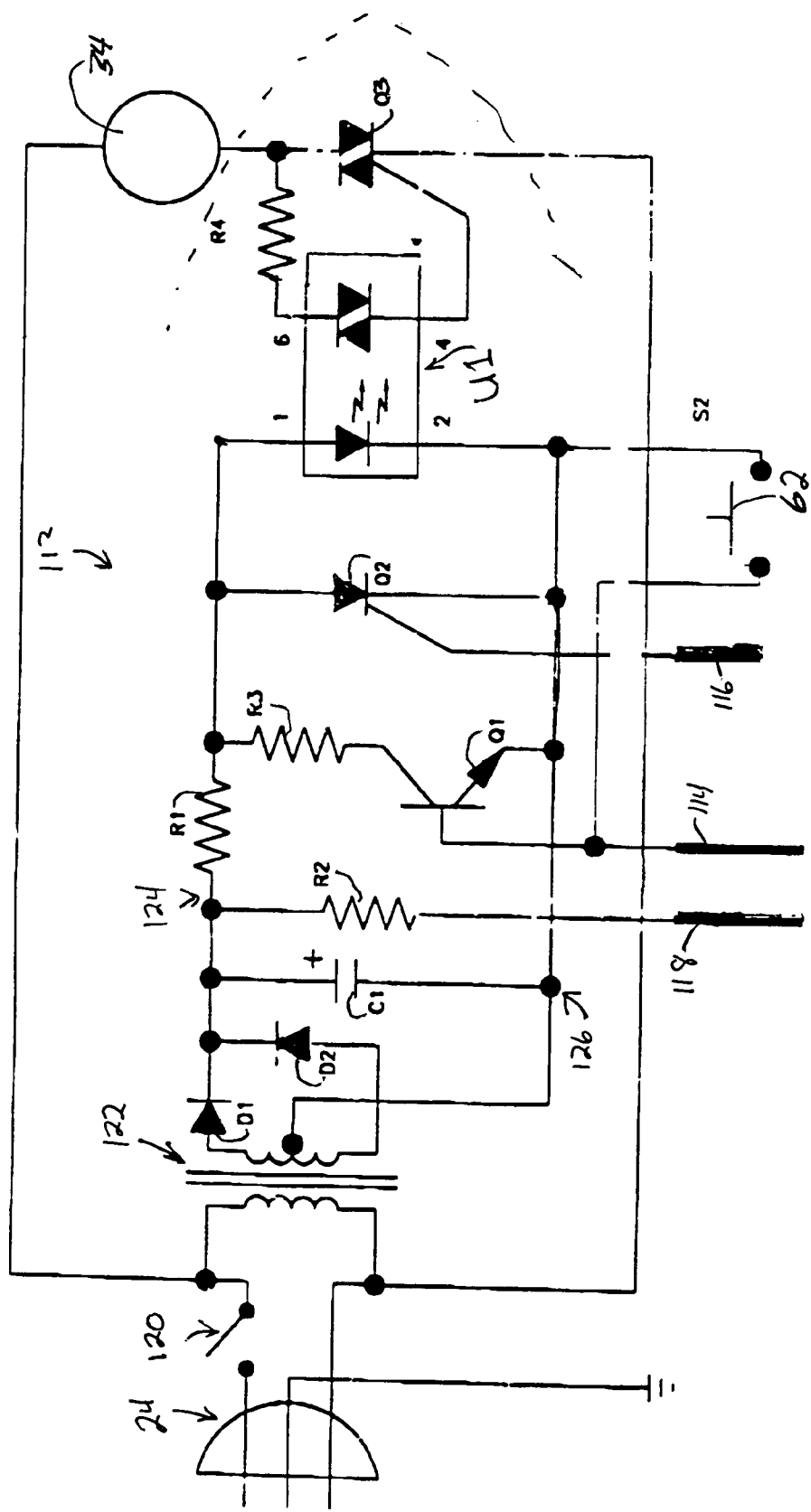
FIG. 10 is a schematic diagram of a preferred embodiment of a control circuit.
Figure 11:
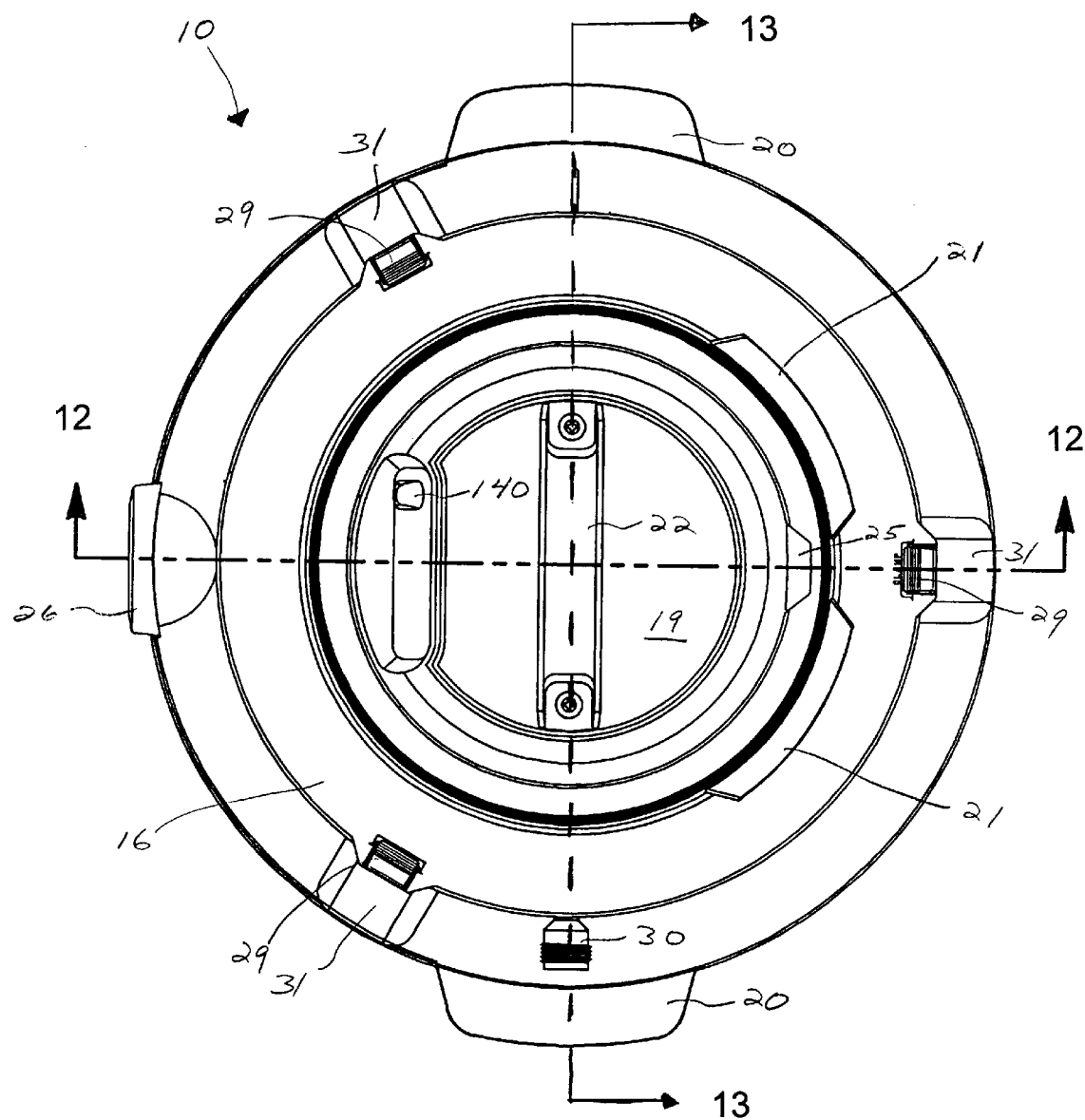
FIG. 11 is a top plan view of a vacuum cleaner of the present invention employing a preferred embodiment of a mechanical shut-off and bypass assembly.

FIG. 10 depicts a schematic diagram of the preferred embodiment of the control circuit 112. The electric cord 24 connects the control circuit 112 to an AC power supply through a main power switch 120 and a step-down transformer 122. The main power switch 120 disconnects power from both the motor 34 and the step-down transformer 122 when opened. In the preferred embodiment, the step-down transformer 122 has a 6 volt secondary winding. Diodes D1 and D2 and a smoothing capacitor C1 rectify and smooth the 6 volt secondary AC voltage, creating a DC voltage across nodes 124 and 126. This provides the DC supply required for the operation of the control circuit 112.

During normal operation of the vacuum, the switch 62 (connected to the depressible actuator 64, not shown) is open and a transistor Q1 and a SCR Q2 are off. A current flows from the node 124 to the node 126 through a resistor R1 and an LED in an optocoupler U1, lighting the LED. This actuates a diac of the optocoupler U1 which, in turn, provides gate current to a gate of a triac Q3. The triac Q3 is thus switched into a low impedance state and allows AC current from the electric cord 24 to reach the motor 34. The AC current causes the motor 34 to operate, allowing normal vacuuming and pumping to take place.

Referring to FIG. 9, in the event that the liquid in the tank 12 rises above the particular liquid level height, a conductive path is formed between the potential-setting electrode 118 and the electrode 114. This allows current to flow from the node 124 (FIG. 10) through a resistor R2 and the potential-setting electrode 118 through the liquid and the electrode 114 to the base of the transistor Q1. The current turns the transistor Q1 on.

Once the transistor Q1 is on, current passes from the node 124 through the resistor R1, a resistor R3 and the transistor Q1 to the node 126 rather than passing through the LED in the optocoupler U1. This turns off the LED in the optocoupler U1, thus turning off the diac and removing the gate drive from the triac Q3. The triac Q3 thus switches to a high impedance state preventing AC current from reaching the motor 34, turning off the motor 34 and preventing any vacuuming or suctioning operations.

When the depressible actuator 64 (shown in FIG. 9) is depressed to command further operation of the motor 34, the switch 62 is closed. Closing the switch 62 connects the base of the transistor Q1 to the node 126, eliminating the base drive therefore and turning the transistor Q1 off. With the transistor Q1 off, current again flows from the voltage node 124 through the resistor R1 to the LED in the optocoupler U1, turning on the diac of the optocoupler U1 and the triac Q3. The motor 34 is therefore turned on, as commanded.

When the liquid eventually reaches the further electrode 116, current flows from the node 124 through the resistor R2 and the electrodes 116 and 118 to the gate of the SCR Q2. This gate current forces the SCR Q2 into a conductive state, shunting the current away from the optocoupler U1 and thereby turning off the triac Q3 to stop the motor 34. Once the gate of the SCR Q2 is activated, the SCR Q2 latches in the conductive state and the optocoupler U1 remains disabled until the liquid level in the tank 12 is manually lowered below the further liquid level height and the main power switch 120 is opened. This action removes the gate drive from and the forward bias across the SCR Q2 to turn off same and thus resets the control circuit 112.

In the preferred embodiment, the control circuit is isolated from the AC power source. This is achieved at the input side by the step-down transformer 122, and at the output side by the optocoupler U1. This isolation prevents leakage currents from being introduced into the liquid in the tank.

Alternatively, the switch 62, the further electrode 116, the transistor Q1 and the resistor R3 could be replaced by a timing mechanism coupled to the SCR Q2. Once the liquid level in the tank 12 rises to the particular liquid level, the timing mechanism is actuated for a specific period of time. The motor 34 continues to operate while the timing mechanism is engaged, allowing the user to lower the level of liquid in the tank 12 by removing the vacuum nozzle from the liquid while the pump continues to expel the contents of the tank 12. If the liquid level is not below the particular liquid level height when the period measured by the timing mechanism expires, the timing mechanism provides gate current to the gate of the SCR Q2, latching it in the conductive state. This, as noted above, shunts current from the optocoupler U1 and latches the motor 34 off. If the liquid level falls below the particular liquid level height when the period expires, the timing mechanism disengages and resets, thereby allowing continued operation of the rotor 34.

Referring now to FIGS. 11–27, an alternative embodiment of the present invention is illustrated. The embodiment includes an actuator mechanism 130, a toggle member 132, a switch 134, a float transmission rod 136, and a float 138.

Figure 14:
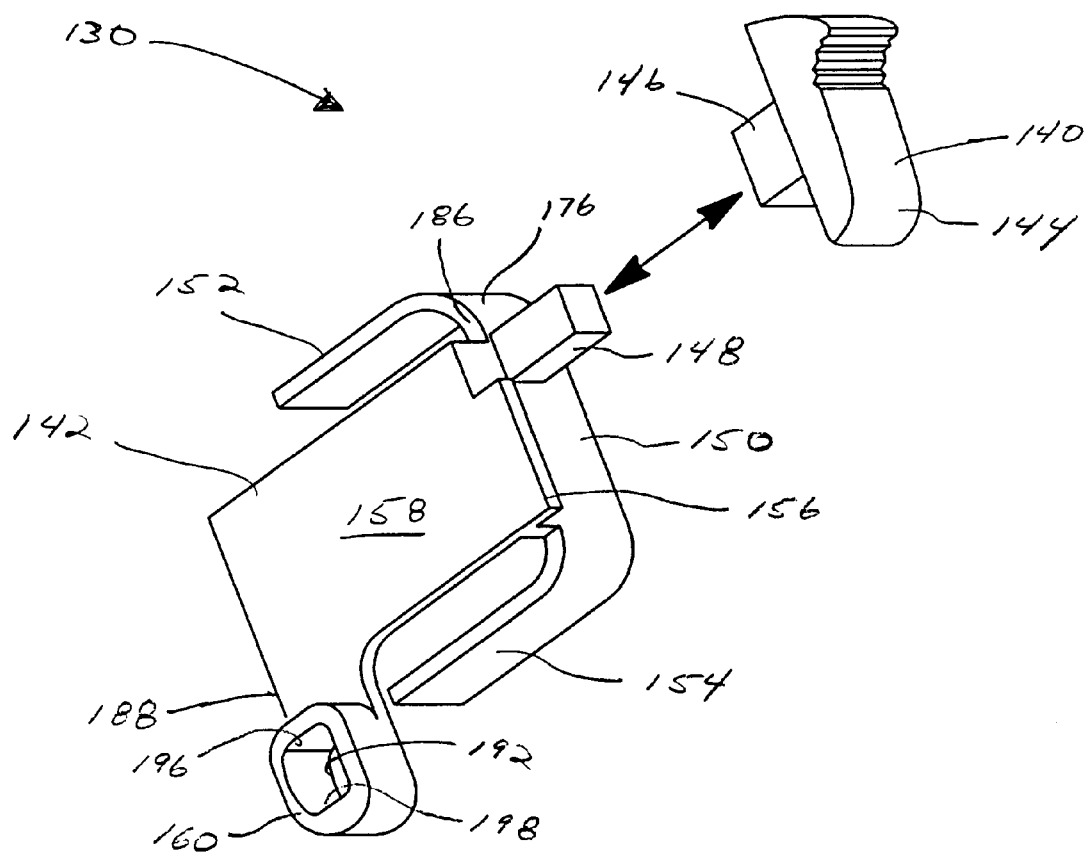
FIG. 14. is a perspective view of a linkage and a toggle actuator of an actuator mechanism.

FIGS. 14–23 illustrate the actuator mechanism 130 and the toggle member 132 in greater detail. Referring to FIG. 14, the actuator mechanism 130 includes a toggle actuator 140 and a linkage 142. The toggle actuator 140 has an engageable portion 144 and a hollow stem coupler 146. The linkage 142 includes an actuator stem 148, a leaf connection member 150, an upper leaf spring 152, a lower leaf spring 154, a standoff 156, a linkage web 158, and a female coupling member 160. The actuator stem 148 is fitted within the stem coupler 146 and moves with the toggle actuator 140. In the preferred embodiment, all of the elements of the toggle member 132 and the actuator mechanism 130 are made of plastic. The toggle member 132 and the toggle actuator 140 are preferably made from acrylonitrile-butadiene styrene copolymer ("ABS"). The linkage 142 is preferably made from a polyamide polymer (e.g. nylon).

Figure 20:
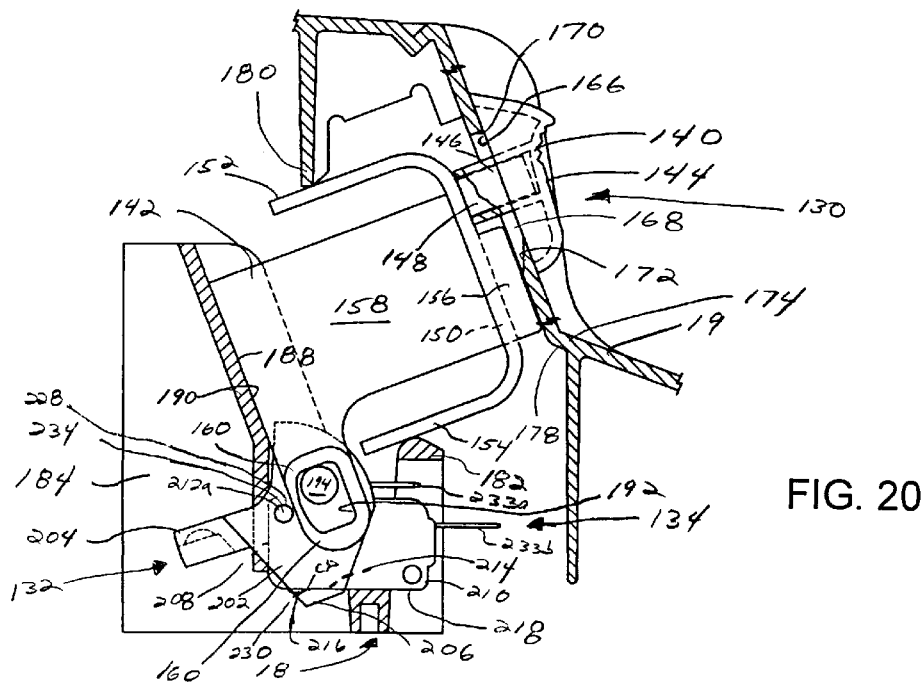
FIG. 20 is a partial view, partially in section, of the actuator mechanism, the toggle member, and the switch of the mechanical shut-off and bypass assembly in an "ON" position.
Figure 22:
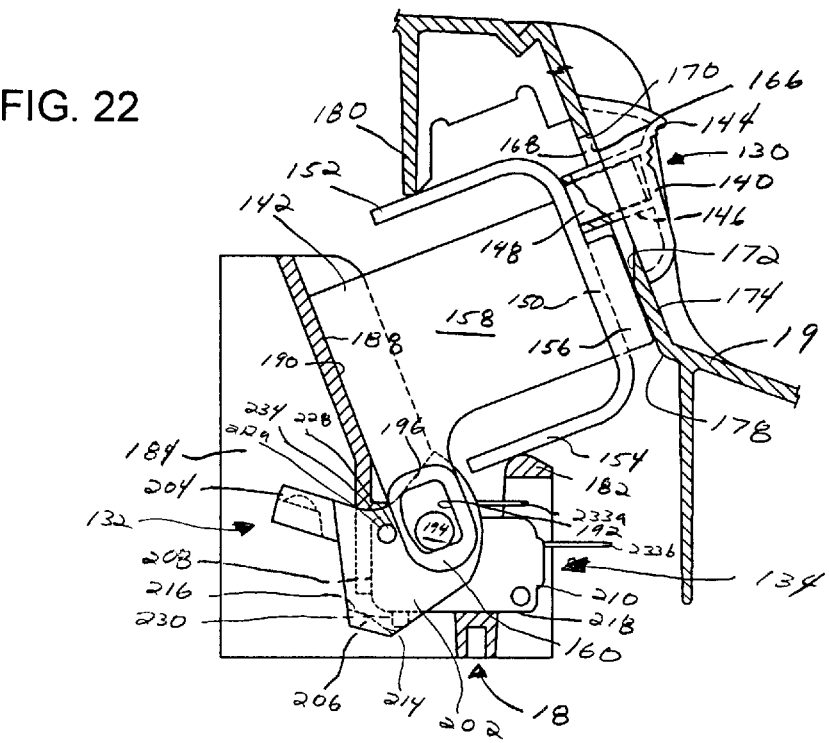
FIG. 22 is a partial view, partially in section, of the actuator mechanism, the toggle member, and the switch in the "OFF" position.

As seen in FIG. 20, an actuator slot 166 of the cover 19 is defined by a pair of sidewalls 168, a top lip 170, and a bottom lip 172. The engageable portion 144 of the toggle actuator 140 is disposed on an outer surface 174 of the cover 19. The stem coupler 146 of the toggle actuator 140 extends inwardly through the actuator slot 166.

The actuator stem 148 extends away from a front side 176 (FIG. 14) of the leaf connection member 150, as does the standoff 156. A leading edge of the standoff 156 abuts an inner surface 178 of the cover 19 (FIGS. 20–23). Also, in the preferred embodiment, the upper leaf spring 152, the leaf connection member 150, and the lower leaf spring 154 form a single, U-shaped piece (FIG. 14). The legs of the "U" point back and downwardly toward the motor housing 18 (FIGS. 20–23). The upper leaf spring 152 abuts an upper rib 180, formed integrally in the cover 19, and creates a first load.

The lower leaf spring 154 abuts a lower rib 182 which is formed in a switch mounting box 184, and creates a second load. In the preferred embodiment, the first load and the second load are equally balanced. Therefore, when a user releases the toggle actuator 140, the equally balanced loads will return the toggle actuator 140 to a centered position in the actuator slot 166.

Figure 15:
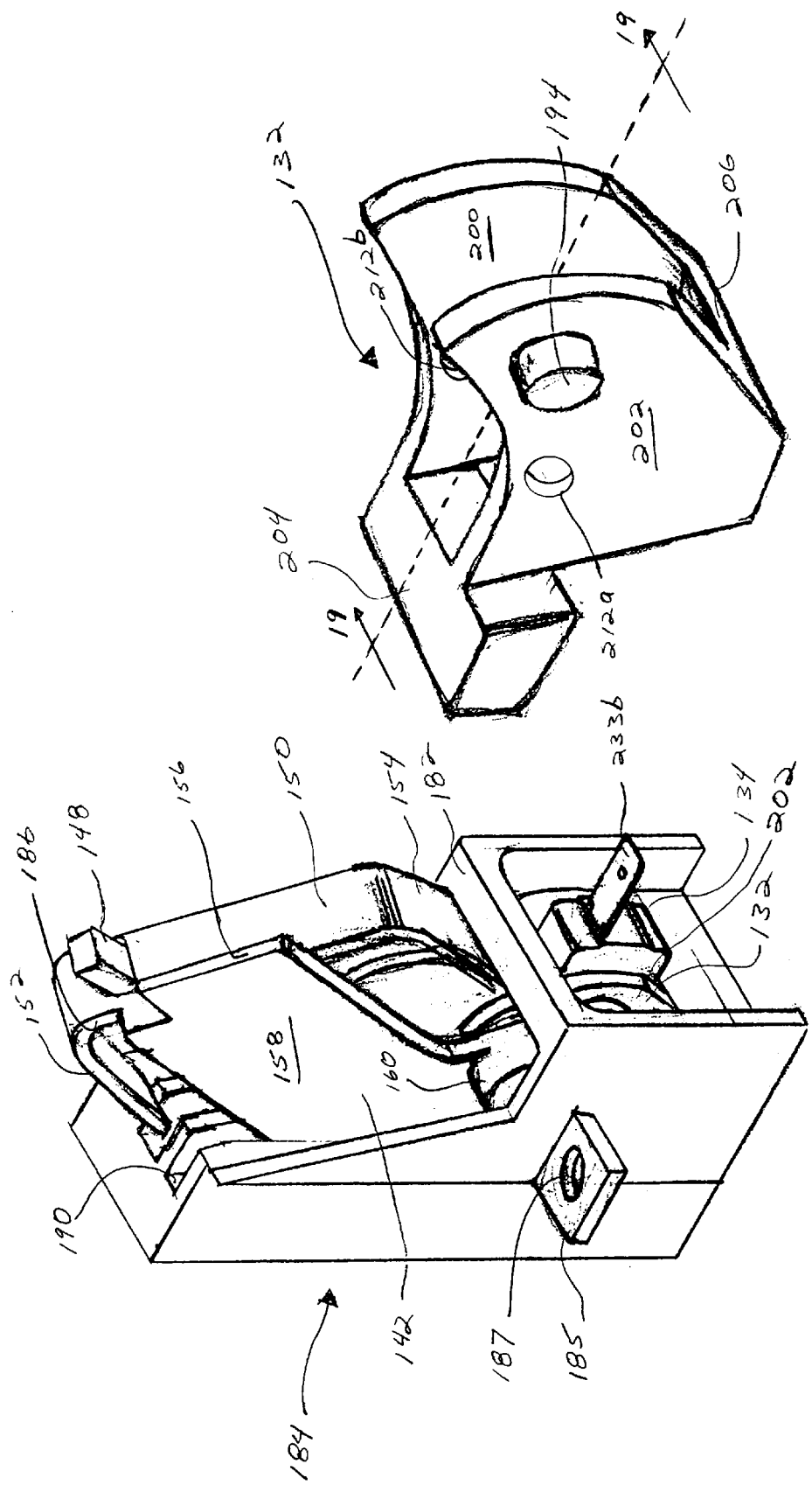
FIG. 15 is a perspective view of the actuator mechanism, a toggle member, and a switch mounted in a switch mounting box.
Figure 16:
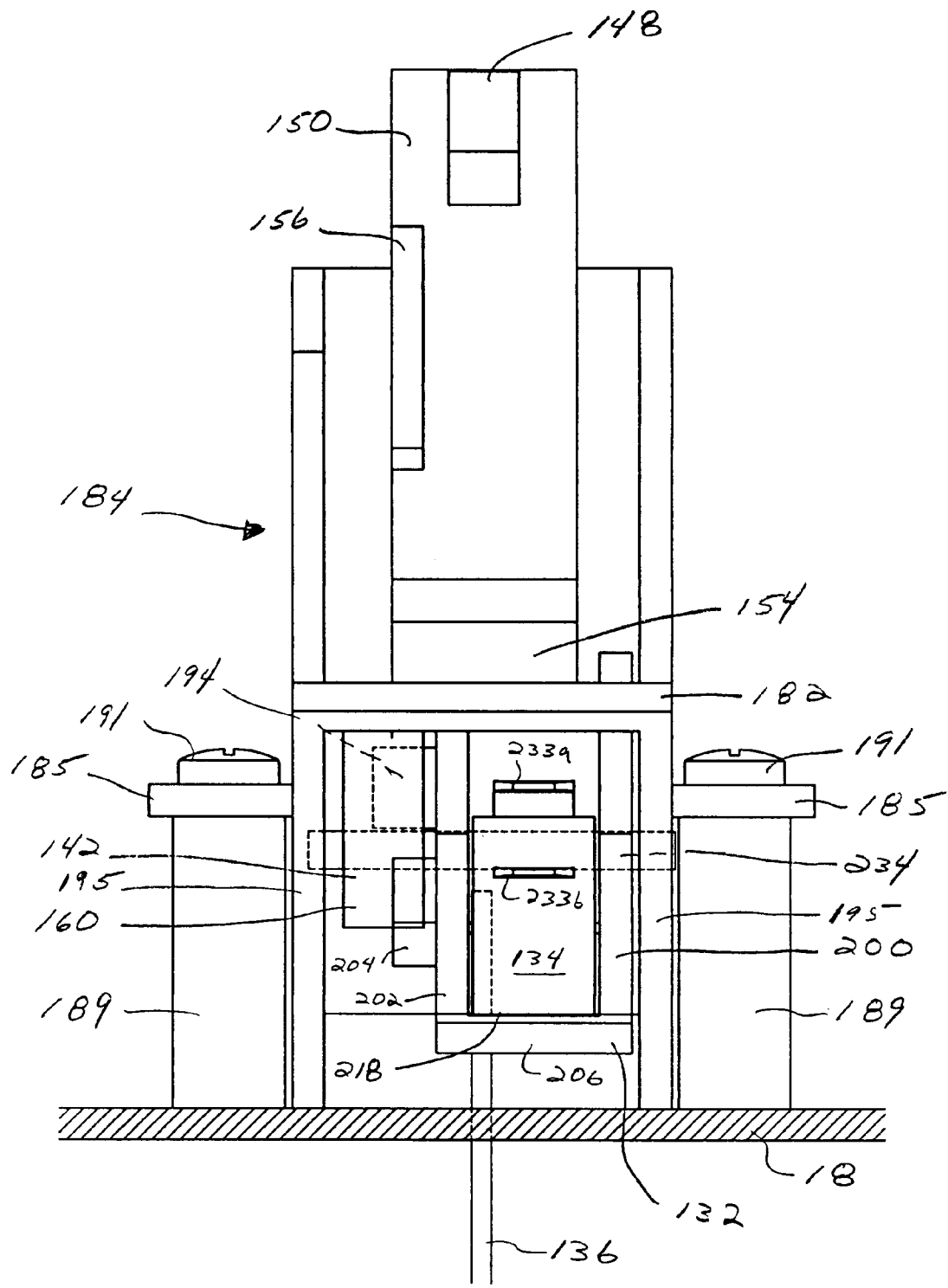
FIG. 16 is a front elevational view of the actuator mechanism, the toggle member, and the switch mounted in the switch mounting box and the switch mounting box attached to a motor housing.

The switch mounting box 184 is a compartment designed to receive and securely hold the switch 134 by any convenient means, as best seen in FIG. 15. The switch mounting box 184 includes a pair of outwardly extending flanges 185 (FIGS. 15 and 16) each of which includes a bolt hole 187 extending therethrough. The motor housing 18 includes a pair of upward extending bolt receiving bosses 189 (FIG. 16). The switch mounting box 184 is secured to the motor housing 18 by bolts 191 which extend through the bolt holes 187 and are secured within threaded bores in the bolt receiving bosses 189.

The linkage web 158 is connected to a sidewall 186 of the leaf connection member 150 and extends backward in the same direction as the leaf springs 152, 154, as best seen in FIGS. 14 and 15. The linkage web 158 has a back end 188 that abuts a base surface 190 of a channel formed integrally in the switch mounting box 184 (FIGS. 15 and 20–23). The female coupling member 160 is disposed at a lower end of the back end 188 and is substantially thicker than the linkage web 158. The extra thickness of the female coupling member 160 provides additional strength and reduces the possibility of breakage that may arise due to repetitive use of the linkage 142.

A boss slot 192 extends through the female coupling member 160. The toggle member 132 (FIG. 16) has a boss 194 which is disposed within the boss slot 192 (FIGS. 20–23). Defining the top and bottom of the boss slot 192 is an upper flange portion 196 and a lower flange portion 198, respectively (FIG. 14). The upper and lower flange portions 196, 198 do not displace the boss 194 in any substantial fashion when the toggle actuator 140 is at rest. However, as will be explained in detail below, when the toggle actuator 140 is engaged, either the upper or lower flange portion 196, 198 engages the boss 194 to move the toggle member 132 to the desired position.

Figures 18, 19:
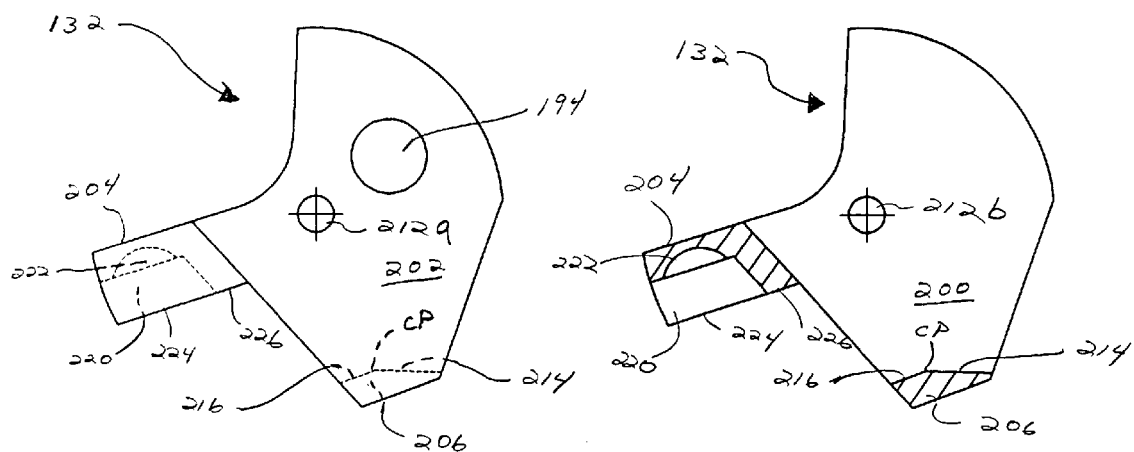
FIG. 18 is a side elevational view of the toggle.
FIG. 19 is a sectional view of the toggle taken along the line 19—19 in FIG. 17.

Referring now to FIGS. 17–19, the toggle member 132 includes integrally-formed elements including the boss 194, first and second sidewalls 200 and 202, a rod receiving extension 204, and a locking brace 206 spanning the distance between the sidewalls 200, 202. When the toggle member 132 is assembled together with the switch mounting box 184, the first and second sidewalls 200, 202 are disposed on opposite sides of the switch 134 between first and second ends 208, 210 thereof (FIGS. 15, 16 and 20–23). The second sidewall 202 is disposed between the switch 134 and the linkage 142. The sidewalls 200, 202 include aligned bores 212a, 212b, respectively, disposed near the first end 208 of the switch 134 (FIG. 17). The boss 194 extends outwardly from the second sidewall 202 into the boss slot 192 of the female coupling member 160 (FIGS. 16, 17 and 20–23).

The locking brace 206 is disposed beneath the first end 208 of the switch 134. As seen specifically in FIGS. 18 and 19, the locking brace 206 includes a ramp portion 214 and a locking portion 216. The ramp portion 214 is angled such that when the toggle member 132 is rotated fully counterclockwise as seen in FIG. 20, the ramp portion 214 lies flush against a bottom surface 218 of the switch 134 (this condition is also shown in FIG. 16). Additionally, the locking portion 216 intersects with the ramp portion 214 at a point CP (FIGS. 18 and 19). In the preferred embodiment, the included angle between the ramp portion 214 and the locking portion 216 is approximately 158 degrees, although this dimension may vary from such value, as will be apparent to one of ordinary skill in the art.

Figures 24, 25:
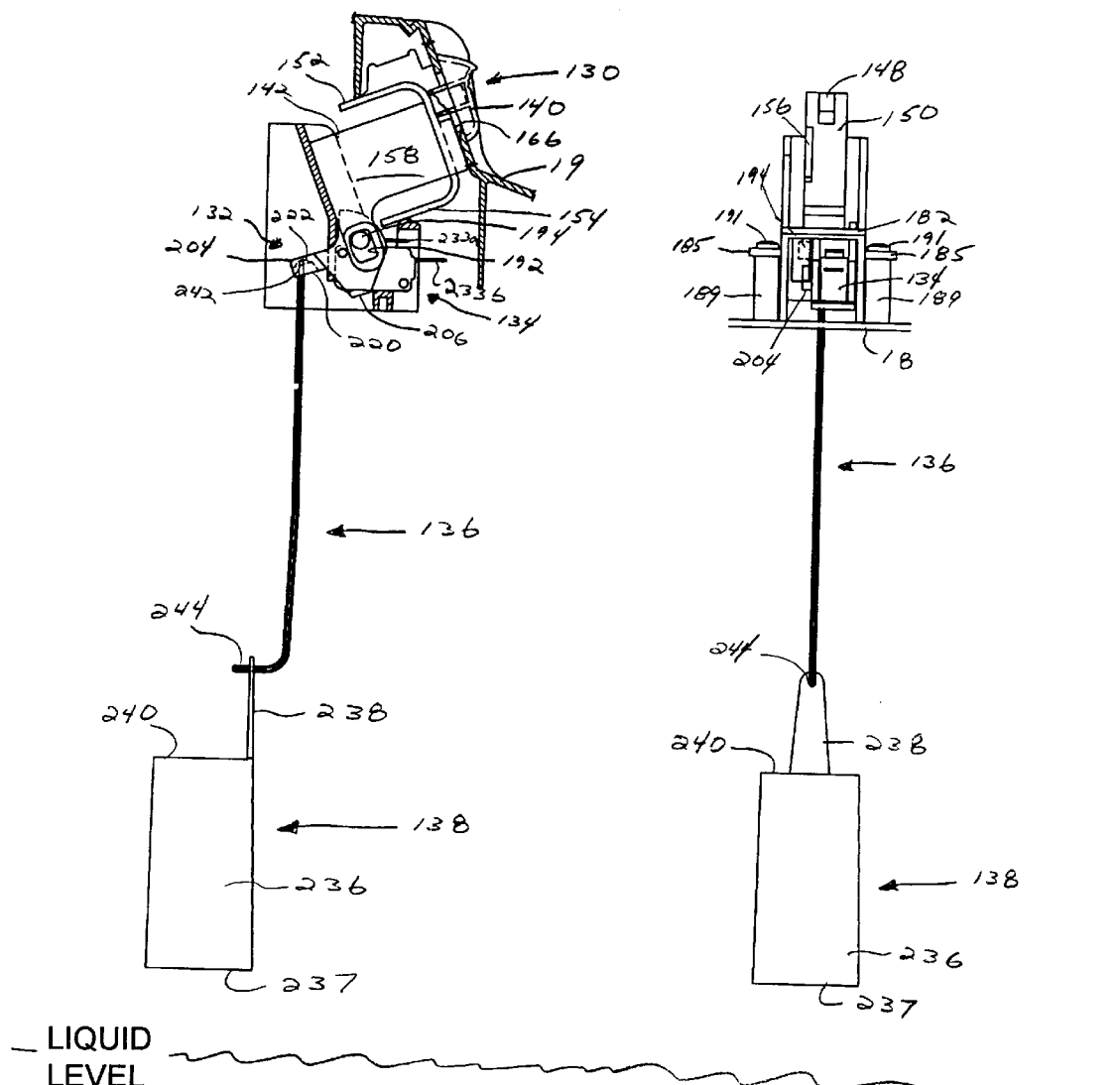
FIG. 24 is a front elevational view of the mechanical shut-off and bypass assembly in an "ON" position.
FIG. 25 is a side elevational view of the mechanical shut-off and bypass assembly in an "ON" position.

Referring again specifically to FIGS. 17 and 20–23, the rod receiving extension 204 is disposed behind the first end 208 of the switch 134 spanning the distance between the sidewalls 200, 202 and further extends outwardly beyond the sidewall 202. As seen in FIGS. 18 and 19, the rod receiving extension 204 defines a guide opening 220 and a semi-circular rod receiving cup 222 above the guide opening 220. The rod receiving cup 222 and the guide opening 220 together receive the float transmission rod 136 (FIG. 25).

Referring now to FIGS. 15, 16 and 20–23, the switch 134 is a standard electrical microswitch and includes an axle bore 228, a momentary actuator 230, an internal spring 232, and a pair of electrodes 233a, 233b. In the preferred embodiment, a Unimax Model #TFCJV4SP004AY made by C&K is used. The switch 134 is securely seated in the switch mounting box 184, and the axle bore 228 is disposed near the first end 208 of the switch 134. The switch 134 is normally in the "OFF" position. To turn the switch 134 "ON", the actuator 230 must be depressed. When the actuator 230 is released, the internal spring 232 pushes the actuator 230 outward, returning the switch 134 to the normally "OFF" position.

An axle 234, best seen in FIG. 16, has ends disposed in a pair of opposing walls 195 of the switch mounting box 184 and extends through the aligned bores 212a, 212b in the first and second sidewalls 200, 202 of the toggle member and the axle bore 228 of the switch 134. The axle 234 acts as an axis of rotation for the toggle member 132.

Figure 12:
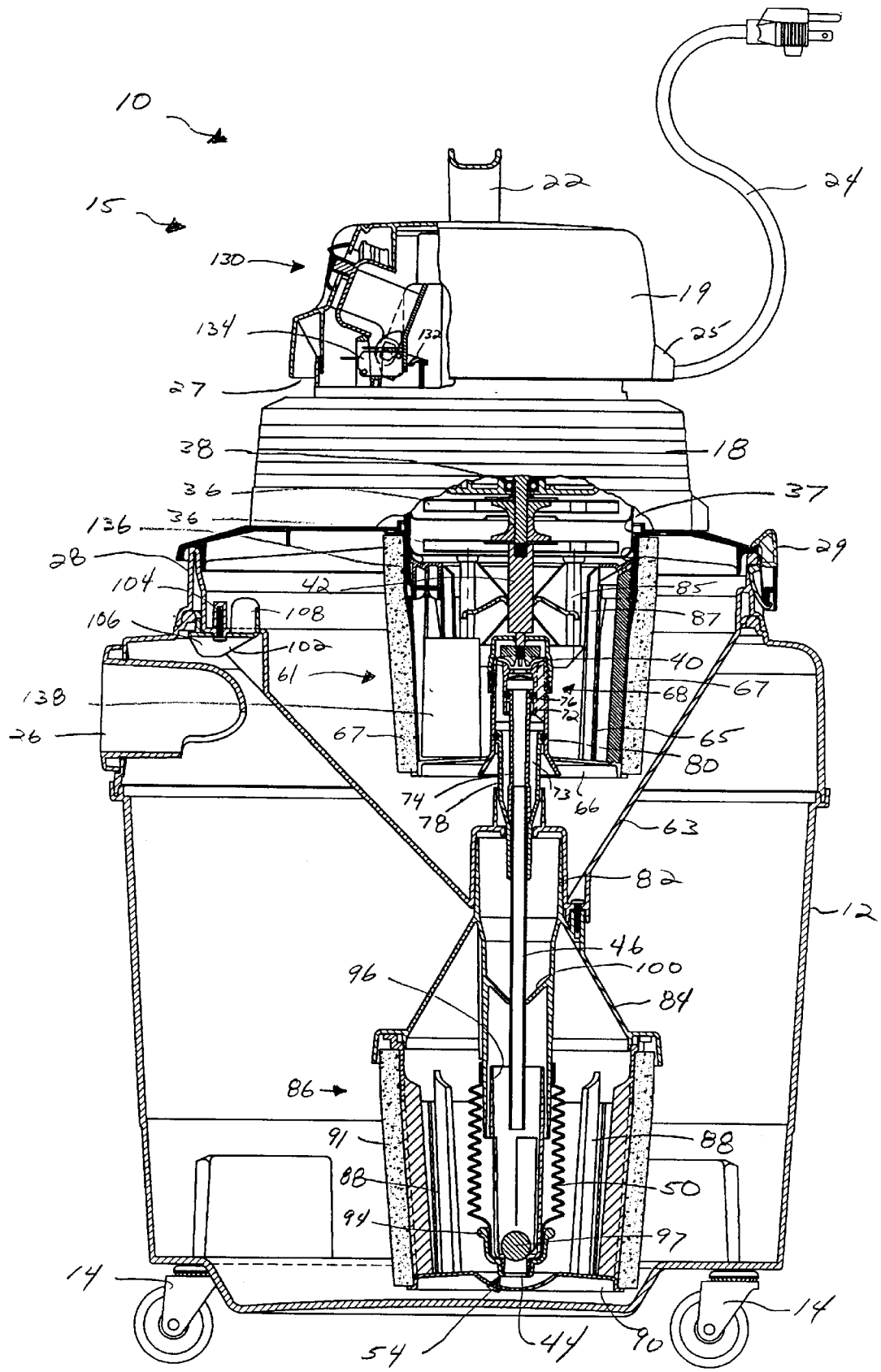
FIG. 12 is a view similar to FIG. 4 showing the preferred embodiment of the mechanical shut-off and bypass assembly.
Figure 13:
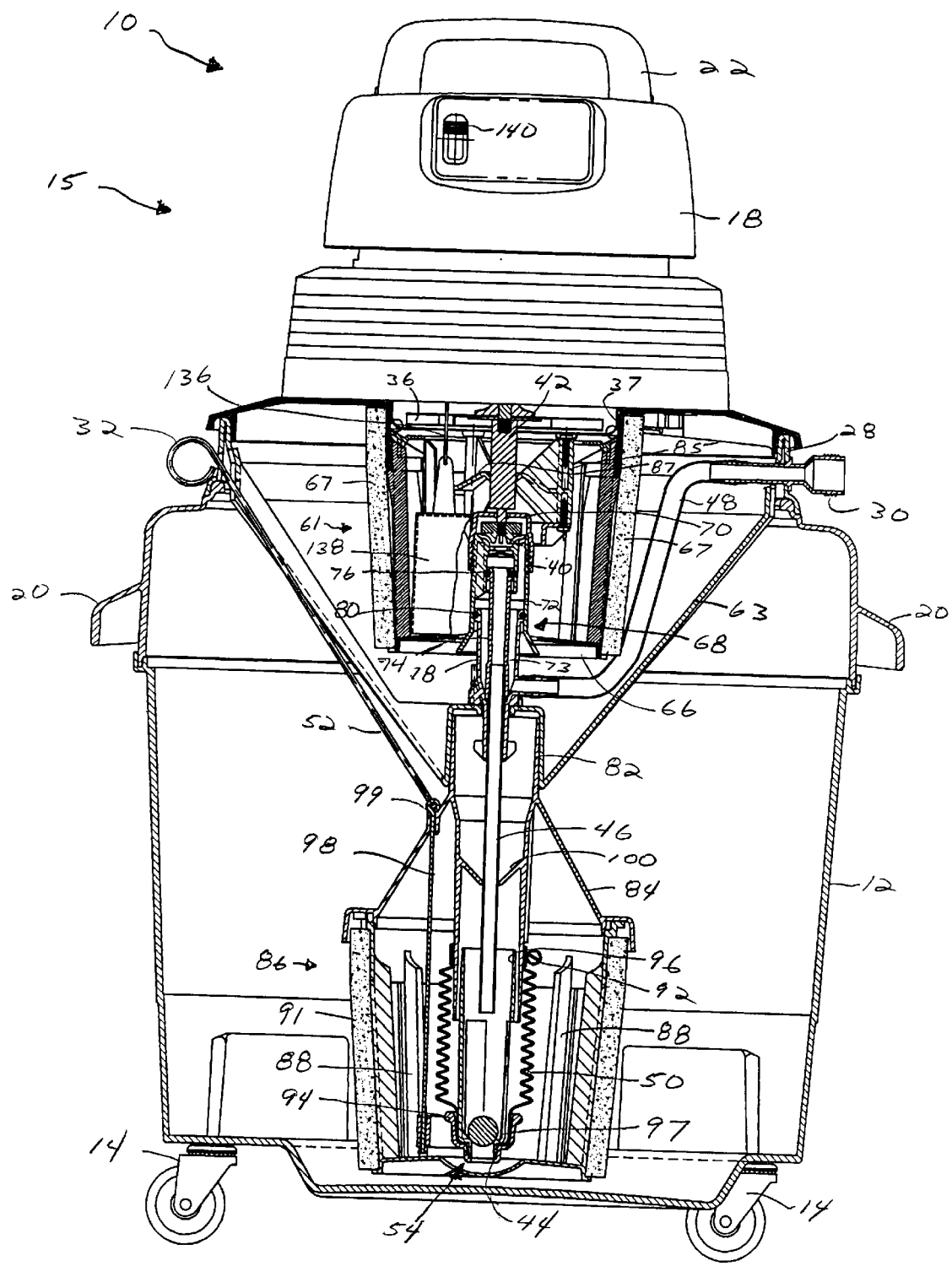
FIG. 13 is a view similar to FIG. 5 showing the preferred embodiment of the mechanical shut-off and bypass system.

Referring now to FIGS. 12 and 24–27, the float 138, which may be hollow and made of any suitable material, is disposed within the lid cage 61. The float 138 includes a float body 236 and an upwardly extending rod cooperating extension 238. The float body 236 rests on the plate 66 when there is no liquid in the tank 12 (FIG. 12).

The float transmission rod 136 has a top end 242 and a bottom end 244. The bottom end 244 is retained within a hole in the rod cooperating extension 238. Alternatively, the bottom end 244 need not be connected to the rod cooperating extension 238, but may instead seat in a groove or slot formed in the rod cooperating extension 238 and still function properly. The top end 242 of the float transmission rod 136 extends into the guide opening 220 of the rod receiving extension 204. Preferably, although not necessarily, the top end 242 is not connected to the rod receiving extension 204 in any manner.

The float transmission rod 136 moves in an unrestricted, non-contained linear up-and-down path in the preferred embodiment. However, other embodiments are envisioned in which the float transmission rod 136 would travel in a linear up-and-down path in a contained channel or guidance slot.

FIGS. 20–23 illustrate different phases of the working relationship between the actuator mechanism 130, the toggle member 132, and the switch 134.

FIG. 20 illustrates the switch 134 in an "ON" position with the toggle actuator 140 at rest and centered in the actuator slot 166. As described above, the upper and lower leaf springs 152, 154 maintain the toggle actuator 140 in this centered position in the actuator slot 166. In the "ON" position, the toggle member 132 is rotated counterclockwise and the locking brace 206 is engaging the actuator 230.

Figure 21:
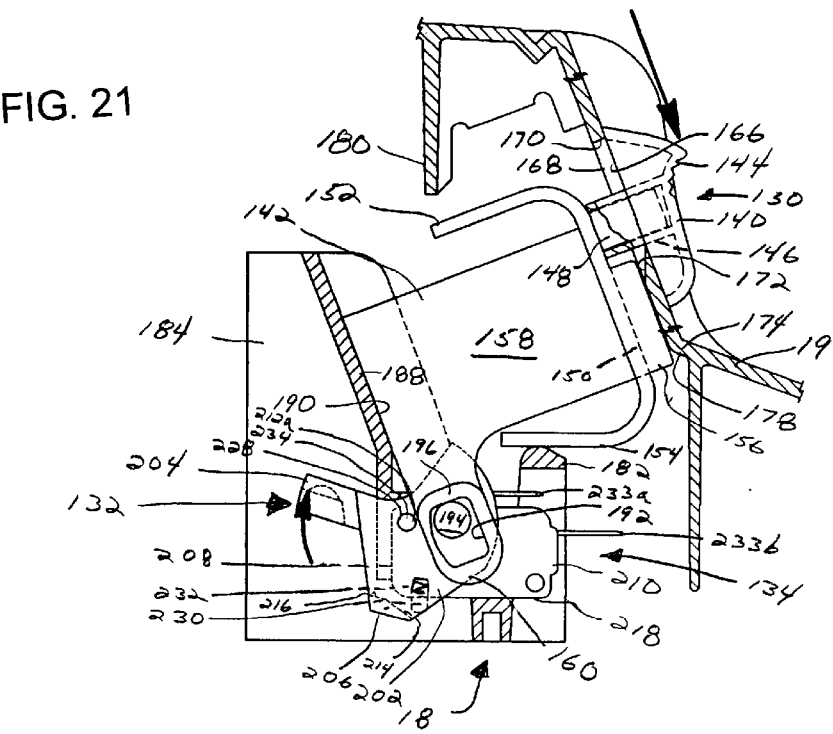
FIG. 21 is a partial view, partially in section, of the actuator mechanism, the toggle member, and the switch transitioning from the "ON" to an "OFF" position.

FIG. 21 illustrates the toggle member 132 in transition from the "ON" to the "OFF" position. In the transition phase illustrated, the user exerts a downward force on the engageable portion 144 of the toggle actuator 140. The downward force is transmitted through the linkage 142 and moves the boss slot 192 downwardly until the upper flange portion 196 of the boss slot 192 engages the boss 194. Continued downward force moves the upper flange portion 196 further downward, which in turn moves the boss 194 downward and rotating the toggle member 132 clockwise around the axle 234. The clockwise rotation of the toggle member 132 moves the locking brace 206 out of engagement with the actuator 230. The compressed internal spring 232 pushes the actuator 230 outward and turns off the switch 134, which in turn shuts off the motor 34. The bottom lip 172 of the actuator slot 166 acts as a stop on the stem coupler 146 of the toggle actuator 140 and keeps the user from pushing the boss 194 too far downward.

Also as the toggle actuator 140 is moved downwardly during the transition from "ON" to "OFF", the upper leaf spring moves out of contact with the upper rib 180 of the switch mounting box 184 and the lower leaf spring 154 is compressed against the lower rib 182. As a result, when the user releases the engageable portion 144 of the toggle actuator 140, the net upward force developed on the leaf connection member 150 causes the actuator mechanism 130 to move upward. The upward movement of the actuator mechanism 130 continues until the forces imposed on the leaf connection member 150 by the upper and lower leaf springs 152, 154 are balanced once again. At that point (FIG. 22), the toggle actuator 140 is centered again in the actuator slot 166, and the boss slot 192 is no longer in engagement with the boss 194 due to the geometry of the boss slot 192. The actuator 230 is pushed downwardly by the internal spring 232 causing the switch to assume the "OFF" position and rotating the toggle member 132 clockwise to the position shown.

Figure 23:
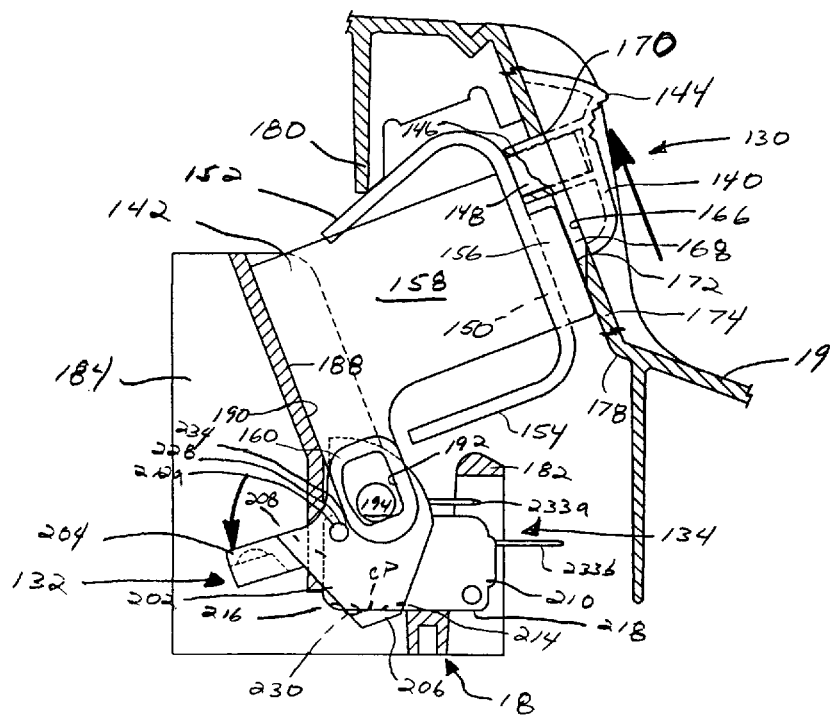
FIG. 23 is a partial view, partially in section, of the actuator mechanism, the toggle member, and the switch transitioning from the "OFF" to the "ON" position.

FIG. 23 illustrates the toggle member 132 in transition from the "OFF" to the "ON" position. In the transition phase illustrated, the user exerts an upward force on the engageable portion 144 of the toggle actuator 140. The upward force is transmitted through the linkage 142 and moves the boss slot 192 upwardly until the lower flange portion 198 of the boss slot 192 engages the boss 194. Continuation of the upward force moves the lower flange portion 198 further upward, in turn moving the boss 194 upwardly and rotating the toggle member 132 counter-clockwise around the axle 234. The counter-clockwise rotation of the toggle member 132 initially moves the ramp portion 214 of the locking brace 206 into engagement with the actuator 230 of the switch 134. As the user further moves the engageable portion 144 upwardly, the actuator 230 begins to move upwardly and the ramp portion 214 of the locking brace 206 slides laterally relative thereto. As the toggle member 132 continues to rotate counter-clockwise, the point CP eventually passes the actuator 230. At this point, the actuator 230 no longer resists the counter-clockwise motion of the locking brace 206, but instead assists such movement and the actuator 230 moves over the surface of the locking portion 216. The locking brace 206 continues to rotate in a counter-clockwise fashion until the ramp portion 214 engages the bottom surface 218 of the switch 134. The components are now in the position shown in FIG. 27.

The upper lip 170 of the actuator slot 166 acts as a stop on the stem coupler 146 of the toggle actuator 140 and keeps the user from pulling the boss 194 too far upward.

Once the ramp portion 214 is flush with the bottom surface 218 of the switch 134, the actuator 230 is latched in the depressed position, and the toggle member 132 remains in the fully counter-clockwise position, owing to the force exerted by the actuator 230 against the locking brace 206.

In the transition from "OFF" to "ON," the upper leaf spring 152 is compressed by the upper rib 180 and the lower leaf spring moves out of contact with the lower rib 182. As a result, when the user releases the engageable portion 144 of the toggle actuator 140, the upper leaf spring 152 transmits a downward force on the leaf connection member 150, causing the actuator mechanism 130 to move downward. The downward movement of the actuator mechanism 130 continues until the forces exerted by the upper and lower leaf springs 152, 154 are again balanced. At that point, the toggle actuator 140 is, once again, centered in the actuator slot 166, and the boss slot 192 is no longer in engagement with the boss 194 (FIG. 20).

FIGS. 24–27 illustrate the operation of the mechanical shut-off and bypass assembly. FIGS. 24 and 25 illustrate the toggle member 132 in the "ON" position (FIG. 20) with the liquid level in the tank 12 below the float 138. When the vacuum cleaner 10 is in use, this is the normal operating configuration. In this configuration, the bottom end 244 of the float transmission rod 136 is resting on the rod cooperating extension 238, and the top end 242 is seated in the rod receiving cup 222. The toggle actuator 140 is centered in the actuator slot 166, and the boss slot 192 is not in engagement with the boss 194.

Figures 26, 27:
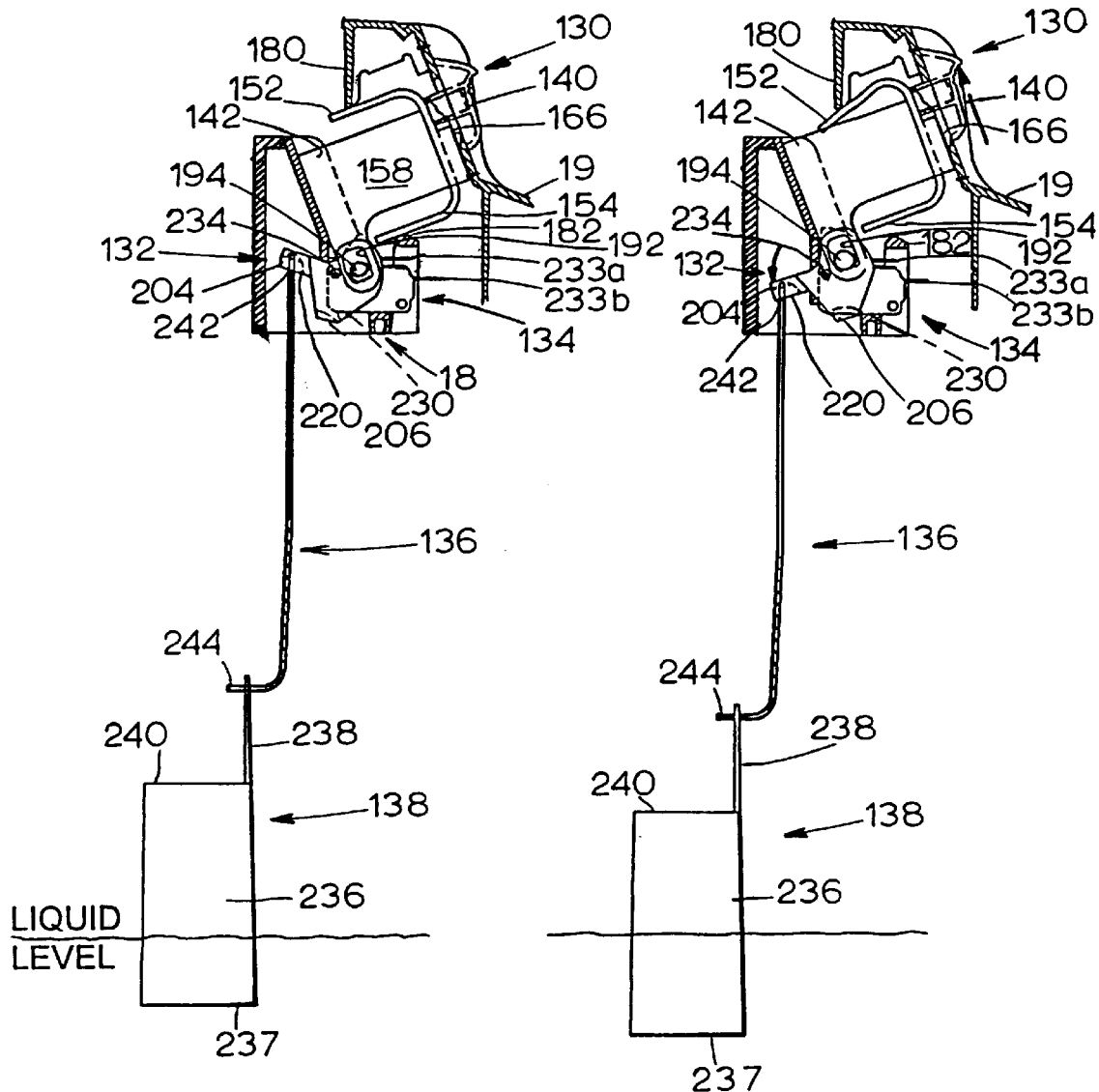
FIG. 26 is a side elevational view of the mechanical shut-off and bypass assembly transitioning to the "OFF" position due to an excessively high water level.
FIG. 27 is a side elevational view of the user bypassing the mechanical shut-off.

FIG. 26 illustrates the situation where the vacuum cleaner 10 is initially on and the liquid level in the tank 12 rises above a pre-set, motor shutoff level causing the liquid to push the float 138 upward. The float 138 pushes the float transmission rod 136 upward, causing the top end 242 of the float transmission rod 136 to push the rod receiving extension 204 of the toggle member 132 upward. This upward movement causes the toggle member 132 to rotate clockwise, eventually taking the locking brace 206 out of engagement with the actuator 230 of the switch 134, and as a consequence, shutting off the motor 34. At this point, the user has the option of emptying the tank 12 by mechanically bypassing the float shut-off or by removing the upper vacuum assembly is and physically emptying the tank 12.

To mechanically bypass the float shut-off, the user pushes upward on the toggle actuator 140 (FIG. 27). As discussed previously, the linkage 142 pulls up on the boss 194, rotating the toggle member 132 counter-clockwise, and depressing the actuator 230. This turns the motor 34 back "ON". However, when the motor 34 is turned back "ON", the user has to continue to hold the toggle actuator 140 up until the liquid level is below the pre-set, motor shut-off level; otherwise, the motor 34 will shut off again. This is due to the fact that to keep the motor 34 "ON" the user is actually forcing the float 138 downward against the upward force of the liquid. Once the liquid level is reduced below the preset, motor shut-off level, the user can release the toggle actuator 140 and the motor 34 will remain "ON". Then, the user may continue normal operation of the vacuum cleaner 10.

If, on the other hand, the user decides to physically empty the tank 12, the user must first remove the upper vacuum assembly 15, and then, lift or tip the tank 12, emptying the contents of the tank 12 therefrom. Assuming that the user is not moving the toggle actuator 140 upwardly during such time, the motor 34 will remain off.

The mechanical shut-off and bypass assembly employs a number of design features to prevent the toggle member 132 from unintentionally rotating counter-clockwise and re-engaging the actuator 230. One design feature is the lack of a connection between the rod receiving extension 204 and the float transmission rod 136. If the float transmission rod 136 were connected to the rod receiving extension 204, the weight of the rod 136 would pull the toggle member 132 downward when the lid 16 is lifted upward. In the present invention, the rod receiving extension 204 and the float transmission 136 separate from each other when the upper vacuum assembly 15 is lifted upward.

Another design feature is the force of the internal spring 232 of the depressible actuator 230. If the toggle member 132 were to rotate counter-clockwise while the upper vacuum assembly 15 was being lifted upward, the motor 34 would remain "OFF" because the toggle member 132 is not capable of generating enough force to overcome the outward force of the internal spring 232. Consequently, the depressible actuator 230 will not be depressed.

The vacuum cleaner of the present invention has significant advantages over prior vacuum cleaners. By providing a pump to remove liquid from the tank, liquid can be emptied easily into drains at a variety of heights. Driving the pump impeller off of the same motor which drives the air impeller significantly reduces the cost of the vacuum cleaner over designs which require a separate motor for the pump. By locating the pump in the tank directly below the air impeller (s), the pump impeller can be simply and efficiently driven off a single axle connected to the air impeller. Removability of portions of the pump, including intake tube, provides significant efficiency when the vacuum cleaner is used on dry material. Attaching the removable portions of the pump to a tank extension, which is removably mounted to the edge of the vacuum tank, permits easy removal and reinstallation of the pump components from the tank.

The electrical and mechanical shut-off and bypass systems of the present invention also provide significant advantages. Both the electrical and mechanical systems of the present invention automatically shut off the motor when the liquid level in the vacuum cleaner tank reaches a preset motor shut-off level. Both the electrical and the mechanical systems allow the user to then bypass the vacuum cleaner shut-off and continue to pump liquid out of the tank without requiring the user to lift or tilt the tank to empty it.

The foregoing detailed description has been given for clearness of understanding only, and no unnecessary limitations should be understood therefrom, as modifications would be obvious to those skilled in the art.

We claim:

1. A mechanical shut-off and bypass assembly for controlling application of power to a motor, comprising:
   a switch having a first position in which power is provided to the motor and a second position in which power to the motor is interrupted;
   a toggle member which engages said switch to move said switch to the first or second position;
   a user operated actuator mechanism for engaging the toggle member to move the switch to the first or the second position; and
   a shut-off mechanism for engaging the toggle member to move the switch from the first position to the second position independent of the user operated actuator mechanism;
   wherein the user operated actuator mechanism is operable in a bypass mode, in which the user operated actuator mechanism engages the toggle member to move the switch from the second position to the first position, thereby to counteract the shut-off mechanism.

2. The mechanical shut-off and bypass assembly of claim 1, wherein the toggle member includes a locking brace having a ramp portion and a locking portion.

3. The mechanical shut-off and bypass assembly of claim 2, wherein the switch includes an actuator which is engageable by the locking brace and is latched by the locking portion.

4. The mechanical shut-off and bypass assembly of claim 1, wherein the actuator mechanism comprises an upper leaf spring, a lower leaf spring, a leaf connection member spanning between and connecting the upper and lower leaf spring and an actuator stem attached to the leaf connection member wherein the upper and lower leaf springs center the actuator stem in a slot.

5. The mechanical shut-off and bypass assembly of claim 1, wherein the actuator mechanism includes a female coupling member having an upper flange portion and a lower flange portion and further defining a boss slot, wherein the toggle member includes a sidewall and a boss connected to the sidewall and extending outward from the toggle member and into the boss slot and wherein neither the upper nor lower flange portion of the female coupling member engages the boss when the actuator mechanism is centered.

6. The mechanical shut-off and bypass assembly of claim 1, in which the first position of the switch is a released position and the second position of the switch is a depressed position.

7. The mechanical shut-off and bypass assembly of claim 6, wherein the toggle member is movable between an on position, in which the toggle member does not engage the switch and the switch is in the released position, and an off position, in which the toggle member engages the switch to move the switch to the depressed position.

8. The mechanical shut-off and bypass assembly of claim 7, in which the toggle member is mounted for pivotable movement with respect to the switch between the on position and the off position.

9. The mechanical shut-off and bypass assembly of claim 1, in which the toggle member comprises an extension portion, and the shut-off mechanism engages the extension portion of the toggle member to move the switch from the first position to the second position.

10. The mechanical shut-off and bypass assembly of claim 9, in which the shut-off mechanism comprises a movable float and a float transmission rod having a top end for engaging the extension portion of the toggle member and a bottom end for engaging the float.

11. The mechanical shut-off and bypass assembly of claim 8, in which the switch is biased toward the released position.

12. The mechanical shut-off and bypass assembly of claim 11, in which the toggle member comprises a locking brace having a ramp portion and a locking portion.

13. The mechanical shut-off and bypass assembly of claim 12, in which the ramp portion is angled with respect to the locking portion, and the ramp portion intersects the locking portion at a point CP.

14. The mechanical shut-off and bypass assembly of claim 13, in which the switch engages the locking portion of the of the locking brace when the toggle member is in the on position, and a force exerted by the spring-biased switch biases the toggle member toward the on position.

15. A mechanical shut-off and bypass assembly for controlling application of power to a motor, the assembly comprising:
   a switch having an actuator biased toward an extended position, in which power is provided to the motor, the actuator being movable to a released position, in which power to the motor is interrupted;
   a toggle member which is movable between an on position, in which the toggle member engages and holds the actuator in the depressed position, and an off position, in which the toggle member is spaced from the actuator so that the actuator is in the released position;

a user operated actuator mechanism engaging the toggle member and operable to move the toggle member between the on position and off position;

an automatic shut-off mechanism for engaging the toggle member, the shut-off mechanism generating a first force which acts to move the toggle member from the on position to the off position;

wherein the user operated actuator mechanism is operable to generate a second force which acts to move the toggle member from the off position to the on position, the second force being greater than the first force.

16. The assembly of claim 15, in which the toggle member comprises a boss, and in which the user operated actuator mechanism comprises a female coupling member defining a boss slot for receiving the boss.

17. The assembly of claim 16, in which the toggle member further comprises an extension portion, and the shut-off mechanism engages the extension portion.

18. The assembly of claim 17, in which the shut-off mechanism comprises a float and a float transmission rod, the float transmission rod having a top end for engaging the extension portion of the toggle member and a bottom end for engaging the float.

19. A mechanical shut-off and bypass assembly for use in a vacuum cleaner having a tank for receiving liquid and dry material and a motor, the mechanical shut-off and bypass assembly comprising:

a switch having a first position in which power is provided to the motor and a second position in which power to the motor is interrupted;

a toggle member which is engageable with the switch to move the switch to the first position or the second position;

a user operated actuator mechanism for engaging the toggle member, the user operated actuator being operable in a first direction, which manipulates the toggle member so that the switch is in the first position, and a second direction, which manipulates the toggle member so that the switch is in the second position;

a shut-off mechanism for engaging the toggle member to move the switch from the first position to the second position when the liquid in the tank reaches a pre-set shut-off level;

wherein the user operated actuator mechanism is operable in a manual bypass mode, in which the user operated actuator mechanism is moved in the first direction so that the toggle member moves the switch from the second position to the first position, thereby to counteract the shut-off mechanism.

20. The mechanical shut-off and bypass assembly of claim 19, in which the shut-off mechanism comprises a float disposed in the tank and positioned at the preset shut-off level, the float being movable in response to liquid present at the pre-set shut-off level, and a float transmission rod having a top end for engaging the toggle member and a bottom end for engaging the float.

* * * * *